(12) United States Patent
Ishikawa et al.

(10) Patent No.: US 6,686,389 B2
(45) Date of Patent: Feb. 3, 2004

(54) 2,3-DIHYDROBENZOFURAN DERIVATIVES

(75) Inventors: Akira Ishikawa, Shizuoka-ken (JP); Yoshiaki Kato, Shizuoka-ken (JP); Kunio Tamura, Shizuoka-ken (JP); Yoshiaki Takashima, Shizuoka-ken (JP); Osamu Cynshi, Shizuoka-ken (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/121,663

(22) Filed: Apr. 15, 2002

(65) Prior Publication Data

US 2002/0156296 A1 Oct. 24, 2002

Related U.S. Application Data

(62) Division of application No. 09/424,456, filed as application No. PCT/JP98/02248 on May 22, 1998.

(30) Foreign Application Priority Data

May 23, 1997 (JP) ............................................. 9/170889

(51) Int. Cl.$^7$ .................... A61K 31/335; C07D 305/12; C07D 303/00

(52) U.S. Cl. ........................ 514/462; 549/330; 549/332

(58) Field of Search ................. 549/330, 332; 514/462

(56) References Cited

U.S. PATENT DOCUMENTS

| 3,946,048 A | | 3/1976 | Fischer et al. | |
|---|---|---|---|---|
| 4,727,086 A | | 2/1988 | Lavielle et al. | |
| 5,091,533 A | | 2/1992 | Belanger et al. | |
| 5,574,178 A | * | 11/1996 | Tamura et al. | 549/462 |
| 5,789,436 A | | 8/1998 | Kato et al. | |
| 6,103,753 A | * | 8/2000 | Cynshi et al. | 514/443 |
| 6,133,279 A | | 10/2000 | Cynshi et al. | |

FOREIGN PATENT DOCUMENTS

| EP | 0 868 913 A1 | 10/1998 |
|---|---|---|
| GB | 2 221 680 A | 2/1990 |
| JP | 8-109179 | 4/1996 |
| WO | WO 97/17066 A1 | 5/1997 |
| WO | WO 97/41844 A1 | 11/1997 |
| WO | WO 97/49388 A1 | 12/1997 |
| WO | WO 98/34646 A2 | 8/1998 |

OTHER PUBLICATIONS

Agarwal et al, "Renal tubular epithelial cels mimic endothelial cells upon exposure to oxidized LDL", *Am J Physiol* 271 (4 Pt 2):F814–23 (1996).
Drukker et al, "Failure of Antioxidant Therapy to Attenuate Interstitial Disease in Rats with Reversible Nephrotic Syndrome", *J Am Soc Nephrol* 9(2):243–251 (1998).
Fujimoto et al, "New alkyl–hydroxy–benzofuran derivative lipoxidase inhibit useful allergic inflammation, bronchial asthma, rheumatism disease, psoriasis", WPI/Derwent 51(52):XP002009524 (1995).
Hammond et al, "2,3–Dihydro–5–benzofuranols as Antioxidant–Based Inhibitors of Leukotriene Biosynthesis", *J Med Chem* 32(5):1006–1020 (1989).
Hammond et al, "Antioxidant–Based Inhibitors of Leukotriene Biosynthesis. The Discovery of 6–[1–[2–(Hydroxymethyl)phenyl]–1–propen–3–yl]–2,3–dihydro–5–benzofuranol, a Potent Topical Antiinflammatory Agent", *J Med Chem* 33(3):908–918 (1990).
Hirano et al, "The Lowering Effect of Probucol on Plasma Lipoprotein and Proteinuria in Puromycin Aminonucleoside–Induced Nephrotic Rats", *Nephron* 58(1):95–100 (1991).
Holding et al, "Failure of a 21–Aminosteroid Antioxidant to Ameliorate Cisplatin–Induced Nephrotoxicity", *Hum Exp Toxicol* 10(5):323–526 (1991).
Konya et al, "Lack of effect of antioxidant therapy during renal ischemia and reperfusion in dogs", *Experientia* 49(3):235–237 (1993).
Lavake et al, "Chemical weed control studies in sugar beets", Chem. Abstract Caplus 83:2075 RN 55218–93–4.
Lee et al, "Dietary antioxidant inhibits lipoprotein oxidation and renal injury in experimental focal segmental glomerulosclerosis", *Kidney Int* 51(4):1151–1159 (1997).
Mabile et al, "α–tocopherol and trolox block the early intracellular events (TBARS and calcium rises) elicited by oxidized low density lipoproteins in cultured endothelial cells", *Free Radic Biol Med* 19(2):177–187 (1995).

(List continued on next page.)

Primary Examiner—Alan L. Rotman
Assistant Examiner—Binta Robinson
(74) Attorney, Agent, or Firm—Browdy and Neimark, P.L.L.C.

(57) ABSTRACT

2,3-Dihydrobenzofuran derivatives of general formula (1):

wherein $R_1$ represents a hydrogen atom or an acyl group; $R_2$, $R_3$ and $R_4$ represent a hydrogen atom, a lower alkyl group or a lower alkenyl group; $R_5$ and $R_6$ combine to form a cycloalkyl group or a saturated heterocyclic group containing one or more oxygen atoms or sulfur atoms, provided that $R_2$ and $R_3$ can not simultaneously represent a t-butyl group, or optically active isomers or pharmaceutically acceptable salts thereof are useful as therapeutic or prophylactic agents for various renal diseases and as organ preservatives.

23 Claims, No Drawings

OTHER PUBLICATIONS

Modi et al, "Effects of probucol in renal function and structure in rats with subtotal kidney ablation", *J Lab Clin Med* 120(2):310–317 (1992).

Paller et al, "Oxygen free radicals in ischemic acute renal failure in the rat", *J Clin Invest* 74(4):1156–1164 (1984).

Rehan et al, "Evidence for the Role of Oxygen Radicals in Acute Nephrotoxic Nephritis", *Lab Invest* 51(4):396–403 (1984).

Takematsu et al, "Processes for the preparation of novel urea derivatives as herbicides", Chem Abstract Caplus 107:236509 RN 111577–09–4 (1987).

Thakur et al, "Evidence suggesting a role for hydroxyl radical in puromycin aminonucleoside–induced proteinuria", *Kidney Int* 34(4):494–499 (1988).

Van den Branden et al, "Effect of vitamin E on antioxidant enzymes, lipid peroxidation products and glomerulosclerosis in the rat remnant kidney", *Nephron* 76(1):77–81 (1997).

Yokota et al, "Preparation of condensed heterocyclic derivatives as weedkillers", Chem Abstract Caplus 120:323604 RN 155009–5–3 (1994).

* cited by examiner

2,3-DIHYDROBENZOFURAN DERIVATIVES

CROSS-REFERENCE TO RELATED APPLICATIONS

This application is a division of U.S. application Ser. No. 09/424,456, filed Nov. 23, 1999, which is a §371 of international application PCT/JP98/02248, filed May 22, 1998, both of which are herein incorporated by reference.

BACKGROUND OF THE INVENTION

1. Field of the Invention

The present invention relates to therapeutic agents for renal diseases or organ preservatives containing a 2,3-dihydrobenzofuran derivative as an active ingredient, as well as novel 2,3-dihydrobenzofuran derivatives.

2. Prior Art

Kidney is one of organs subjected to the most serious oxidative stress in the living body. The importance of radical injury caused by active oxygen or free radicals in the development and progress mechanism of various renal diseases such as acute renal failure, drug-induced nephropathies, glomerular nephritis, diabetic nephrosis, chronic renal failure, renal transplantation has long been pointed out. In recent years, the role of lipids in cell injury has attracted particular attention (Keane W. F., Lipids and the kidney. Kidney Int., 46:910–920, 1994; Higuchi and Sanaka, "Renal Diseases", Antioxidants—Free radicals and bioprotection (Niki, Shimazaki and Mino, eds.) Gakkai Shuppan Center, 223–229, 1994; Aoyagi, "Therapy with Antioxidants/Scavenger, No. 3, Renal Diseases", Therapeutics, 26:592–596, 1992). However, the effect of antioxidants, particularly lipid-peroxidation inhibitors on renal diseases has not been well explained, and any compound having a useful lipid-peroxidation inhibitory effect as a therapeutic or prophylactic agent for renal diseases or organ preservative has not been reported.

Vitamin E (α-tocopherol) is a naturally occurring potent lipid-peroxidation inhibitor and its use in renal transplantation and renal ischemia models has been reported (Marubayashi, Dohi and Kawasaki, "Renal maintenance and active oxygen", Kidney and Dialysis, 24:785–790, 1988; Takenaka M., Tatsukawa Y., Dohi K., Ezaki H., Matsukawa K., Kawasaki T., Transplantation, 32:137–141, 1981), but its effect is not sufficient. This is because it acts on only surfaces of membranes and lipid of the living body, but cannot produce inhibitory effect against lipid-peroxidation in the interior of membranes and lipids (Niki E., Chem. Phys. Lipids, 44:227–253, 1987). Vitamin E is also expected to endogenously have an inhibitory effect against lipid-peroxidation on surfaces of membranes and lipid, because it endogenously occurs in a significantly large amount (Nakamura, "Absorption, Distribution and Excretion of Vitamin E", Vitamin E—Basic and Clinical Study (Igarashi, eds.), Ishiyaku Shuppan, 33–58, 1985). However, the living body does not have a sufficient protection mechanism against lipid-peroxidation in the interior of membranes and lipids, and therefore, inhibition of lipid-peroxidation in the interior of membranes and lipids seems to have an important effect for treatment and prevention of renal diseases. The effects of use of a lipid-soluble antioxidant, probucol, in various renal disease models have been reported (Modi K. S., Schreiner G. F., Purkerson M. L., J. Lab. Clin. Med., 120:310–317, 1992; Bird J. E., Milhoan K., Wilson C. B., Young S. G., Mundy C. A., Parthasarathy S., Blantz R. C., J. Clin. Invest., 81:1630–1638, 1988; Hirano T., Mamo J. C. L., Nagano S., Sugisaki T., Nephron, 58:95–100, 1991), but such simple phenolic compounds as probucol and butylated hydroxytoluene react with lipid-peroxide radicals at a lower reactivity than α-tocopherol by one or more orders of magnitude (Gotoh N., Shimizu K., Komuro E., Tsuchiya J., Noguchi N., Niki E., Biochem. Biophys. Acta, 1128:147–154, 1992; Burton G. W., Ingold K. U., J. Am. Chem. Soc., 103:6472–6477, 1981) and thus have not shown sufficient protective effect for renal functions.

Thus, a potent cytoprotective agent which inhibits lipid-peroxidation that is difficult to inhibit by Vitamin E seems to be effective for the prevention and treatment of various renal diseases and maintenance of organs.

As such compounds, 4,6-di-t-butyl-2,3-dihydrobenzofuran derivatives were found to show a potent cytoprotective effect on kidney-derived cells (JP 10-72458A/98, WO97/49388), but no report has shown that 2,3-dihydrobenzofuran derivatives having no or only one t-butyl group show such an effect.

DISCLOSURE OF THE INVENTION

As a result of extensive research to solve the above problems, we found that 2,3-dihydrobenzofuran derivatives having specific substituents show a potent cytoprotective effect on kidney-derived cells, and thus accomplished the present invention.

Accordingly, the present invention provides therapeutic agents for renal diseases containing a compound of general formula (1):

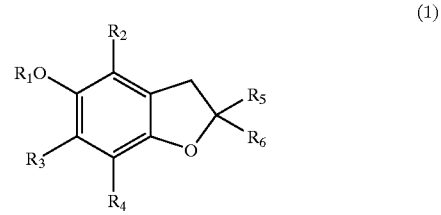

(1)

wherein $R_1$ represents a hydrogen atom or an acyl group, $R_2$, $R_3$ and $R_4$, which may be identical or different, each represents a hydrogen atom, a lower alkyl group or a lower alkenyl group, and $R_5$ and $R_6$, which may be identical or different, each represents a hydrogen atom, an optionally substituted alkyl group, an optionally substituted alkenyl group, an optionally substituted alkynyl group or an optionally substituted aryl group, or $R_5$ and $R_6$ combine to form a cycloalkyl group or a saturated heterocyclic group containing one or more oxygen atoms, sulfur atoms or alkyl-substituted nitrogen atoms, provided that $R_2$ and $R_3$ cannot simultaneously represent a t-butyl group, or an optically active isomer or a pharmaceutically acceptable salt thereof as an active ingredient.

The present invention also provides organ preservatives containing a compound of the above general formula (1) or an optically active isomer or a pharmaceutically acceptable salt thereof as an active ingredient.

The present invention also provides compounds of general formula (1):

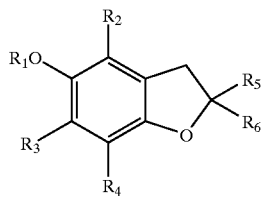

(1)

wherein $R_1$ represents a hydrogen atom or an optionally substituted acyl group, $R_2$, $R_3$ and $R_4$, which may be identical or different, each represents a hydrogen atom, a lower alkyl group or a lower alkenyl group, provided that any one of $R_2$ and $R_3$ represents a t-butyl group but both of $R_2$ and $R_3$ cannot represent a t-butyl group, and $R_5$ and $R_6$, which may be identical or different, each represents a hydrogen atom, an optionally substituted alkyl group, an optionally substituted alkenyl group, an optionally substituted alkynyl group or an optionally substituted aryl group, or $R_5$ and $R_6$ combine to form a cycloalkyl group or a saturated heterocyclic group containing one or more oxygen atoms, sulfur atoms or alkyl-substituted nitrogen atoms, provided that the following cases are excluded where:

$R_4$ represents a 2-propenyl group;

three or more of $R_2$, $R_3$, $R_4$, $R_5$ and $R_6$ simultaneously represent a hydrogen atom;

$R_2$ and $R_4$ simultaneously represent a hydrogen atom and $R_5$ and $R_6$ simultaneously represent a methyl group; and $R_3$, $R_4$, $R_5$ and $R_6$ simultaneously represent a methyl group, or optically active isomers or pharmaceutically acceptable salts thereof.

In one aspect, compounds of the above general formula (1) are represented by general formula (2):

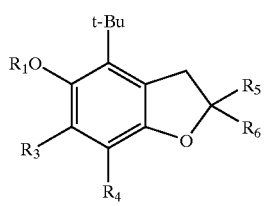

(2)

wherein $R_4$ represents a hydrogen atom or a t-butyl group, and $R_1$, $R_3$, $R_5$ and $R_6$ have the same meanings as defined above.

In another aspect, compounds of the above general formula (1) are represented by general formula (3):

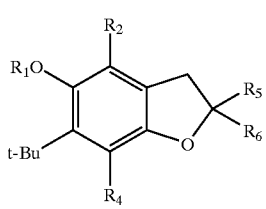

(3)

wherein $R_1$, $R_2$, $R_5$ and $R_6$ have the same meanings as defined above, provided that the total carbon number of $R_2$, $R_5$ and $R_6$ is at least 3.

The present invention also provides compounds of general formula (1):

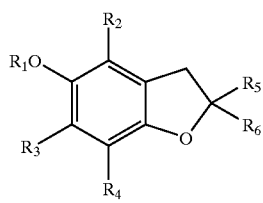

(1)

wherein $R_1$ represents a hydrogen atom or an optionally substituted acyl group, $R_2$ and $R_4$ simultaneously represent a t-butyl group, and $R_3$, $R_5$ and $R_6$ simultaneously represent a hydrogen atom, or optically active isomers or pharmaceutically acceptable salts thereof.

The present invention also provides compounds of general formula (1):

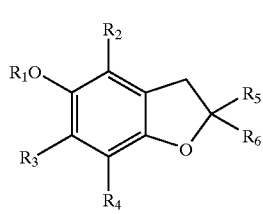

(1)

wherein $R_1$ represents a hydrogen atom or an optionally substituted acyl group, $R_2$, $R_3$ and $R_4$, which may be identical or different, each represents a hydrogen atom, a lower alkyl group or a lower alkenyl group, provided that any of $R_2$ and $R_3$ cannot represent a t-butyl group, and $R_5$ and $R_6$, which may be identical or different, each represents an optionally substituted alkyl group containing 1 to 10 carbon atoms, an optionally substituted alkenyl group containing 2 to 10 carbon atoms, an optionally substituted alkynyl group containing 2 to 10 carbon atoms or an optionally substituted aryl group containing 6 to 10 carbon atoms, or $R_5$ and $R_6$ combine to form a cycloalkyl group containing 3 to 8 carbon atoms or a saturated 5–12 membered heterocyclic group containing 1 to 3 oxygen atoms, sulfur atoms or alkyl-substituted nitrogen atoms, provided that the following cases are excluded where:

$R_2$, $R_3$ and $R_4$ are independently selected from a hydrogen atom or a methyl group;

$R_2$ and $R_3$ each represents a hydrogen atom, a methyl group, an isopropyl group or a 2-propenyl group and $R_5$ and $R_6$ simultaneously represent a methyl group;

$R_2$ represents an isopropyl group and $R_3$ and $R_4$ simultaneously represent a methyl group; and $R_2$ represents an n-butyl group and $R_3$, $R_5$ and $R_6$ simultaneously represent a methyl group, or optically active isomers or pharmaceutically acceptable salts thereof.

MOST PREFERRED EMBODIMENTS OF THE INVENTION

In the definition of substituents for compounds of general formula (1), $R_1$ represents a hydrogen atom or an optionally substituted acyl group. Examples of the acyl group include those containing 1 to 7 carbon atoms, such as acetyl, formyl, propyonyl, trimethylacetyl and benzoyl groups. Examples of the substituted acyl group include benzyloxycarbonyl, aminoacetyl, N-methylaminoacetyl and N,N-dimethylaminoacetyl groups. However, $R_1$ preferably represents a hydrogen atom.

$R_2$, $R_3$ and $R_4$ represent a hydrogen atom, a lower alkyl group or a lower alkenyl group. The lower alkyl group means a straight or branched alkyl group containing 1 to 6 carbon atoms, such as methyl, ethyl, n-propyl, i-propyl, n-butyl, s-butyl and t-butyl groups. The lower alkenyl group means a straight or branched alkenyl group containing 2 to 6 carbon atoms, such as vinyl, allyl, butenyl and pentenyl groups.

While not wishing to be bound by any particular theory, it is believed that compounds of the present invention represented by general formula (1) inhibit lipid-peroxidation within membranes and lipids in the living body to exhibit a potent cytoprotective effect on kidney-derived cells as a result of the proper hydrophobicity conferred on the benzene ring in general formula (1) by the $R_2$, $R_3$ and $R_4$ groups adjacent or proximal to the hydroxyl group or acyloxy group represented by $R_1O$—. Thus, $R_2$, $R_3$ and $R_4$ preferably represent a group capable of conferring proper hydrophobicity.

Therefore, one or two of $R_2$, $R_3$ and $R_4$ preferably represent an alkyl or alkenyl group containing 3 to 6 carbon atoms, more preferably a branched alkyl group containing 3 to 4 carbon atoms, and most preferably a t-butyl group.

In a preferred embodiment, one or two of $R_2$, $R_3$ and $R_4$ represent(s) a branched alkyl or alkenyl group containing 3 to 6 carbon atoms, and the other(s) represent(s) a hydrogen atom. In a more preferred embodiment, one or both of $R_2$ and $R_3$ represent a branched alkyl or alkenyl group containing 3 to 6 carbon atoms, the total carbon number of $R_2$ and $R_3$ is 8 or less, and $R_4$ represents a hydrogen atom. In a most preferred embodiment, one of $R_2$ and $R_3$ represents a t-butyl group, the total carbon number of $R_2$ and $R_3$ is 8 or less, and $R_4$ represents a hydrogen atom. In another preferred embodiment, one or two of $R_2$, $R_3$ and $R_4$ represent(s) a t-butyl group, the other(s) represent(s) a hydrogen atom, and the total carbon number of $R_2$, $R_3$ and $R_4$ is 8 or less.

$R_5$ and $R_6$ may be identical or different and each represents a hydrogen atom, an optionally substituted alkyl group, an optionally substituted alkenyl group, an optionally substituted alkynyl group or an optionally substituted aryl group. This alkyl group means a straight or branched alkyl group containing 1 to 20, preferably 1 to 10, more preferably 1 to 6, and most preferably 2 to 6 carbon atoms, such as methyl, ethyl, n-propyl, i-propyl, n-butyl, s-butyl, t-butyl, pentyl, hexyl, heptyl, octyl, nonyl, or decyl group. The alkenyl group means a straight or branched alkenyl group containing 2 to 20, preferably 2 to 10, and more preferably 2 to 6 carbon atoms, such as vinyl, allyl, butenyl, pentenyl, geranyl, or farnesyl group. The alkynyl group means a straight or branched alkynyl group containing 2 to 20, preferably 2 to 10, and more preferably 2 to 6 carbon atoms, such as ethynyl, propynyl, or butynyl group. The aryl groups means a monovalent aromatic hydrocarbon preferably containing 6 to 20, and more preferably 6 to 10 carbon atoms, such as phenyl, tolyl, xylyl, biphenyl, naphthyl, anthryl, or phenanthyl group.

When $R_5$ and $R_6$ represent an alkyl, alkenyl, alkynyl or aryl group, they may have a substituent such as a halogen atom, a lower alkyl group, a lower alkenyl group, a hydroxyl group, an amino group, a substituted amino group such as dimethylamino, an alkoxy group, an aryloxy group, a nitro group, a trifluoromethyl group, a phenyl group, an acetoxy group, etc. Examples of the halogen atom include chlorine, bromine, fluorine and iodine. Examples of the lower alkyl and lower alkenyl groups include those listed above for $R_2$. Examples of the alkoxy and aryloxy groups include those derived from the alkyl and aryl groups listed above for $R_5$ and $R_6$.

Alternatively, $R_5$ and $R_6$ combine to form a cycloalkyl group or a saturated heterocyclic group containing one or more oxygen atoms, sulfur atoms or alkyl-substituted nitrogen atoms. The cycloalkyl group here means a cycloalkyl group containing 3 to 8, preferably 5 to 8 carbon atoms, such as cyclopropyl, cyclobutyl, cyclopentyl, cyclohexyl, cycloheptyl, or cyclooctyl group. Examples of the saturated heterocyclic group containing oxygen atoms, sulfur atoms or alkyl-substituted nitrogen atoms include saturated 5–12 membered heterocyclic groups containing 1 to 3 such heteroatoms, such as tetrahydropyranyl, tetrahydrothiopyranyl, and N-methylpiperidyl groups.

Compounds of general formula (1) wherein $R_2$ represents a t-butyl group preferably have the following substituents.

$R_1$ is preferably a hydrogen atom or an acetyl, trimethylacetyl, benzyloxycarbonyl, aminoacetyl, N-methylaminoacetyl or N,N-dimethylaminoacetyl group, especially a hydrogen atom or an acetyl, trimethylacetyl or N,N-dimethylaminoacetyl group.

$R_3$ is preferably a hydrogen atom or a methyl, ethyl, n-propyl, i-propyl or i-butyl group, especially a hydrogen atom or an i-propyl group.

$R_4$ is preferably a hydrogen atom or a methyl, n-propyl, i-butyl or t-butyl group, especially a hydrogen atom or a t-butyl group.

$R_5$ is preferably a hydrogen atom or a methyl, ethyl, n-propyl, i-propyl, n-butyl, i-butyl, s-butyl, t-butyl, n-pentyl, benzyl, hydroxymethyl, aminomethyl or N,N-dimethylaminomethyl group, especially a hydrogen atom or a methyl, n-pentyl, benzyl, hydroxymethyl, aminomethyl or N,N-dimethylaminomethyl group.

$R_6$ is preferably a hydrogen atom or a methyl, ethyl, n-propyl, i-propyl, n-butyl, i-butyl, s-butyl, t-butyl, n-pentyl or benzyl group, especially a hydrogen atom or a methyl, n-pentyl or benzyl group.

The cyclic group formed by $R_5$ and $R_6$ is preferably a cyclopentyl, cyclohexyl, cycloheptyl, cyclooctyl, tetrahydropyranyl, tetrahydrothiopyranyl or N-methylpiperidyl group, especially a cyclopentyl, cyclohexyl, cycloheptyl or tetrahydropyranyl group.

Compounds of general formula (1) wherein $R_3$ represents a t-butyl group preferably have the following substituents.

$R_1$ is preferably a hydrogen atom or an acetyl, trimethylacetyl, benzyloxycarbonyl, aminoacetyl, N-methylaminoacetyl or N,N-dimethylaminoacetyl group, especially a hydrogen atom or an acetyl, trimethylacetyl or N,N-dimethylaminoacetyl group.

$R_2$ is preferably a hydrogen atom or a methyl, ethyl, n-propyl, i-propyl, i-butyl, s-butyl, allyl or methallyl group, especially a hydrogen atom or a methyl, n-propyl, i-propyl, i-butyl or s-butyl group.

$R_4$ is preferably a hydrogen atom or a methyl or n-propyl group, especially a hydrogen atom.

$R_5$ is preferably a hydrogen atom or a methyl, ethyl, n-propyl, i-propyl, n-butyl, i-butyl, s-butyl, t-butyl, n-pentyl, benzyl, hydroxymethyl, aminomethyl or N,N- dimethylaminomethyl group, especially a hydrogen atom or a methyl, n-pentyl, benzyl, hydroxymethyl, aminomethyl or N,N-dimethylaminomethyl group.

$R_6$ is preferably a hydrogen atom or a methyl, ethyl, n-propyl, i-propyl, n-butyl, i-butyl, s-butyl, t-butyl, n-pentyl or benzyl group, especially a hydrogen atom or a methyl, n-pentyl or benzyl group.

The cyclic group formed by $R_5$ and $R_6$ is preferably a cyclopentyl, cyclohexyl, cycloheptyl, cyclooctyl, tetrahydropyranyl, tetrahydrothiopyranyl or N-methylpiperidyl group, especially a cyclopentyl, cyclohexyl, cycloheptyl or tetrahydropyranyl group.

In a preferred embodiment, $R_1$ represents a hydrogen atom or an acyl group containing 1 to 7 carbon atoms; one or two of $R_2$, $R_3$ and $R_4$ represent(s) a branched alkyl or alkenyl group containing 3 to 6 carbon atoms while the other(s) represent(s) a hydrogen atom; and $R_5$ and $R_6$ each represents a hydrogen atom or an alkyl group containing 1 to 20 carbon atoms or $R_5$ and $R_6$ combine to form a cycloalkyl group containing 3 to 8 carbon atoms. In a more preferred embodiment, $R_1$ represents a hydrogen atom; one or both of $R_2$ and $R_3$ each represents a branched alkyl or alkenyl group containing 3 to 6 carbon atoms but the total carbon number of $R_2$ and $R_3$ is 8 or less; $R_4$ represents a hydrogen atom; and $R_5$ and $R_6$ each represents a hydrogen atom or an alkyl group containing 1 to 10 carbon atoms or $R_5$ and $R_6$ combine to form a cycloalkyl group containing 3 to 8 carbon atoms. In a most preferred embodiment, $R_1$ represents a hydrogen atom; one of $R_2$ and $R_3$ represents a t-butyl group but the total carbon number of $R_2$ and $R_3$ is 8 or less; $R_4$ represents a hydrogen atom; and $R_5$ and $R_6$ each represents a hydrogen atom or an alkyl group containing 1 to 6 carbon atoms or $R_5$ and $R_6$ combine to form a cycloalkyl group containing 5 to 8 carbon atoms. In another preferred embodiment, $R_1$ represents a hydrogen atom; one or two of $R_2$, $R_3$ and $R_4$ represent(s) a t-butyl group while the other(s) represents) a hydrogen atom but the total carbon number of $R_2$, $R_3$ and $R_4$ is 8 or less; and $R_5$ and R6 each represents a hydrogen atom or an alkyl group containing 1 to 6 carbon atoms or $R_5$ and $R_6$ combine to form a cycloalkyl group containing 5 to 8 carbon atoms.

Compounds of the present invention represented by general formula (1) may have an asymmetric center, therefore may be optically active. The present invention includes not only racemates but also optically active isomers themselves.

Compounds of general formula (1) having some substituents can form an addition salt with an acid or a base. Therefore, the present invention includes pharmaceutically acceptable salts of compounds of general formula (1). Examples of the acid addition salt of the compound of general formula (1) include inorganic salts such as hydrochloride, sulfate, nitrate and phosphate, as well as organic acid salts such as acetate, lactate, oxalate, citrate, tartrate and p-toluenesulfonate. Examples of the base addition salt of the compound of general formula (1) include salts with inorganic bases such as sodium salt, potassium salt, calcium salt, aluminium salt, ammonium salt, as well as organic amine salts.

Preferred examples of the compounds of the present invention are as follows:

4,7-di-t-butyl-5-hydroxy-2,3-dihydrobenzofuran;

4,7-di-t-butyl-5-hydroxy-2-methyl-2,3-dihydrobenzofuran;

4,7-di-t-butyl-5-hydroxy-2-n-octyl-2,3-dihydrobenzofuran;

4,7-di-t-butyl-5-hydroxy-2,2-dimethyl-2,3-dihydrobenzofuran;

6-t-butyl-5-hydroxy-2,2-dimethyl-2,3-dihydrobenzofuran;

6-t-butyl-2,2-di-n-pentyl-5-hydroxy-2,3-dihydrobenzofuran;

6-t-butyl-5-hydroxy-2,3-dihydrobenzofuran-2-spiro-1'-cycloheptane;

6-t-butyl-5-hydroxy-4-(2-propenyl)-2,3-dihydrobenzofuran-2-spiro-1'-cycloheptane;

6-t-butyl-5-hydroxy-4-n-propyl-2,3-dihydrobenzofuran-2-spiro-1'-cycloheptane;

6-t-butyl-5-hydroxy-4-(2-methyl-2-propenyl)-2,3-dihydrobenzofuran-2-spiro-1'-cycloheptane;

6-t-butyl-5-hydroxy-4-(2-methylpropyl)-2,3-dihydrobenzofuran-2-spiro-1'-cycloheptane;

6-t-butyl-5-hydroxy-4-(1-methyl-2-propenyl)-2,3-dihydrobenzofuran-2-spiro-1'-cycloheptane;

6-t-butyl-5-hydroxy-4-(1-methylpropyl)-2,3-dihydrobenzofuran-2-spiro-1'-cycloheptane;

6-t-butyl-5-hydroxy-4-methyl-2,3-dihydrobenzofuran-2-spiro-1'-cycloheptane;

6-t-butyl-4-ethyl-5-hydroxy-2,3-dihydrobenzofuran-2-spiro-1-cycloheptane;

6-t-butyl-5-hydroxy-2,3-dihydrobenzofuran;

6-t-butyl-5-hydroxy-2-methyl-2,3-dihydrobenzofuran;

2,2-diethyl-5-hydroxy-4,6-diisopropyl-2,3-dihydrobenzofuran;

5-hydroxy-2,2-dimethyl-4,6-diisopropyl-2,3-dihydrobenzofuran;

6-t-butyl-5-hydroxy-2,2,4-trimethyl-2,3-dihydrobenzofuran;

6-t-butyl-5-hydroxy-2,2-dimethyl-4-isopropyl-2,3-dihydrobenzofuran; and 4-t-butyl-5-hydroxy-2,2-dimethyl-6-isopropyl-2,3-dihydrobenzofuran.

Therapeutic agents for renal diseases of the present invention can be used as various pharmaceutical compositions comprising a compound of general formula (1) as an active ingredient in combination with a physiologically non-toxic solid or liquid pharmaceutical carrier. These pharmaceutical compositions are formulated and used in various dosage forms depending on the administration route. Dosage forms include tablets, granules, pills, capsules, solutions, syrups, suspensions, emulsions and injections. Suitable pharmaceutical carriers include commonly used excipients, binders, disintegrants, lubricants, coating agents, dissolution-aids, emulsifiers, suspending agents, stabilizers and solvents.

Therapeutic agents for renal diseases of the present invention can be used via oral administration, parenteral administration such as intravenous injection, administration of sustained-release formulations, etc.

Therapeutic agents for renal diseases of the present invention can be used for therapies of various renal diseases such as chronic renal failure, diabetic nephrosis, glomerular nephritis, immunocomplex nephritis, acute renal failure, nephropathies caused by platinum complex-based anticancer agents such as cisplatin or other drugs such as gentamicin, nephropathies caused by agrichemicals such as Paracort, and uremia. Actually desired dosage of compounds of general formula (1) depends on the age, sex and weight of the patient, severity of condition, administration route or other factors, and an effective daily dosage which is normally acceptable is, for example, 1–1000 mg, and preferably 10–500 mg/adult. Such dosage is preferably divided into 1–3 doses per day per patient in need of therapy.

Compounds of general formula (1) can also be used as an active ingredient of organ preservatives. Compounds of general formula (1) can be used as organ preservatives for any organ of humans and animals, such as brain, heart, kidney, pancreas, lung, liver and bone marrow cells, preferably kidney of humans and animals. Compounds of the present invention can be added in a maintenance solution or a perfusion solution to minimize damages of an organ during storage of the organ extracted from a donor for transplantation. Compounds of the present invention can be used to inhibit deterioration of extracted organs and to maintain functions of the organs after transplantation.

When compounds of general formula (1) are used in a maintenance solution required for storing organs, they are preferably dissolved at an effective dose which is normally acceptable such as 1–1000 mg in the maintenance solution at a concentration of, for example, 0.1–10000 mg/L.

The following examples and test examples further illustrate the present invention, but are not construed as limiting the same.

EXAMPLES

Example 1

4,7-Di-t-butyl-5-hydroxy-2,3-dihydrobenzofuran

In a solution of 2.84 g of 4-t-butyl-5-hydroxy-2,3-dihydrobenzofuran [J. Org. Chem. 53, 4135 (1988)] in 10.0 g of t-butyl alcohol and 20 ml of chloroform was added dropwise 10 ml of methane sulfonate under ice-cooling. The mixture was stirred at 0° C. for 15 minutes, then poured into ice water. Then, the mixture was neutralized with a 1N aqueous sodium hydroxide solution and extracted with ethyl acetate. The extracted layers were washed with a saturated aqueous sodium bicarbonate solution, dried over anhydrous magnesium sulfate and then concentrated. The concentrate was purified by silica gel column chromatography (in n-hexane) to give 1.78 g of 4,7-di-t-butyl-5-hydroxy-2,3-dihydrobenzofuran as a white crystal (yield 48%).

$^1$H NMR (60 MHz, CDCl$_3$) δ ppm: 1.29 (s, 9H), 1.41 (s, 9H), 3.35 (t, 2H, J=8.0 Hz), 4.10 (s, 1H), 4.39 (t, 2H, J=8.0 Hz), 6.39 (s, 1H).

Mass: 248 (M$^+$)

Example 2

4,7-Di-t-butyl-5-hydroxy-2-methyl-2,3-dihydrobenzofuran

1) Synthesis of 5-Benzyloxy-4-t-butylbenzofuran

In 200 ml of N,N-dimethylformamide were dissolved 40.0 g of 4-t-butyl-5-hydroxybenzofuran [J. Org. Chem. 53, 4135 (1988)], 43.0 g of benzyl bromide and 28.8 g of potassium carbonate, and the mixture was stirred at room temperature for a whole day and night. After N,N-dimethylformamide was distilled off under reduced pressure, the solution was combined with water and extracted with ethyl acetate. The extracted layers were washed with a saturated aqueous sodium bicarbonate solution, dried over anhydrous magnesium sulfate and then concentrated. The concentrate was purified by silica gel column chromatography (in n-hexane containing 10% ethyl acetate) to give 49.1 g of 5-benzyloxy-4-t-butylbenzofuran as a colorless oil (yield 83%).

$^1$H NMR (60 MHz, CDCl$_3$) δ ppm: 1.57 (s, 9H), 5.06 (s, 2H), 6.86–7.43 (m, 9H)

Mass: 280 (M$^+$).

2) Synthesis of 5-Benzyloxy-4-t-butyl-2-formylbenzofuran

Under ice-cooling, 26.2 ml of phosphorus oxychloride was added dropwise to 17 ml of N,N-dimethylformamide, followed by a solution of 40.0 g of 5-benzyloxy-4-t-butylbenzofuran in 10 ml of N,N-dimethylformamide. After stirring at room temperature for 20 minutes, the mixture was heated at 80° C. for 2 hours. After cooling, the reaction solution was poured into water and extracted with ethyl acetate. The extracted layers were washed with a saturated aqueous sodium bicarbonate solution and then water, dried over anhydrous magnesium sulfate, and then concentrated. The concentrate was purified by silica gel column chromatography (in n-hexane containing 10% ethyl acetate) to give 16.2 g of 5-benzyloxy-4-t-butyl-2-formylbenzofuran as a pale yellow solid (yield 36%).

$^1$H NMR (60 MHz, CDCl$_3$) δ ppm: 1.58 (s, 9H), 5.10 (s, 2H), 7.20–7.48 (m, 7H). 7.92 (s, 1H), 9.76 (s, 1H).

Mass: 308 (M$^+$)

m.p.: 135.7° C.

3) Synthesis of 4-t-Butyl-5-hydroxy-2-methylbenzofuran

A solution of 1.0 g of 5-benzyloxy-4-t-butyl-2-formylbenzofuran in a mixed solvent of 50 ml of ethyl acetate and 2 ml of acetic acid was vigorously stirred with 1.0 g of 10% palladium on carbon for 20 hours in a hydrogen atmosphere. After the palladium on carbon was filtered out, the filtrate was concentrated and the concentrate was purified by silica gel column chromatography (in n-hexane containing 20% ethyl acetate) to give 0.11 g of 4-t-butyl-5-hydroxy-2-methylbenzofuran as a white crystal (yield 17%).

$^1$H NMR (60 MHz, CDCl$_3$) δ ppm: 1.48 (s, 9H), 2.29 (s, 3H), 4.87 (s, 1H). 6.43 (d, 1H, J=8.8 Hz), 6.60 (s, 1H), 6.98 (d, 1H, J=8.8 Hz)

Mass: 204 (M$^+$)

4) Synthesis of 4-t-Butyl-5-hydroxy-2-methyl-2,3-dihydrobenzofuran

Under ice-cooling, 1.4 ml of trifluoroacetic acid was added dropwise to 0.25 g of 4-t-butyl-5-hydroxy-2-methylbenzofuran in 2.8 ml of triethylsilane. After stirring at 0° C. for 15 minutes and then at room temperature for 18 hours, the mixture was poured into ice water and extracted with ethyl acetate. The extracted layers were washed with a saturated aqueous sodium bicarbonate solution, dried over anhydrous magnesium sulfate, and then concentrated. The concentrate was purified by silica gel column chromatography (in n-hexane containing 20% ethyl acetate) to give 0.18 g of 4-t-butyl-5-hydroxy-2-methyl-2,3-dihydrobenzofuran as a white crystal (yield 74%).

$^1$H NMR (60 MHz, CDCl$_3$) δ ppm: 1.40 (d, 3H, J=4.0 Hz), 1.48 (s, 9H), 2.78–3.29 (m, 1H), 3.38–3.78 (m, 1H), 4.42–5.04 (m, 1H), 5.30 (s, 1H), 6.46 (s, 2H).

Mass: 206 (M$^+$)

5) Synthesis of 4,7-Di-t-butyl-5-hydroxy-2-methyl-2,3-dihydrobenzofuran

Under ice-cooling, 3 ml of methanesulfonic acid was added dropwise to a solution of 0.77 g of 4-t-butyl-5-hydroxy-2-methyl-2,3-dihydrobenzofuran in 1.5 g of t-butyl alcohol and 6 ml of chloroform. After stirring at 0° C. for 10 minutes, the mixture was poured into ice water and extracted with ethyl acetate. The extracted layers were washed with a saturated aqueous sodium bicarbonate solution, dried over anhydrous magnesium sulfate and then concentrated. The concentrate was purified by silica gel column chromatography (in chloroform) to give 0.55 g of 4,7-di-t-butyl-5-hydroxy-2-methyl-2,3-dihydrobenzofuran as a white crystal (yield 57%).

$^1$H NMR (60 MHz, CDCl$_3$) δ ppm: 1.29 (s, 9H), 1.41 (d, 3H, J=4.0 Hz), 1.43 (s, 9H), 2.73–3.17 (m, 1H), 3.23–3.73 (m, 1H), 4.38–4.88 (m, 1H), 4.68 (s, 1H), 6.42 (br, 1H).

Mass: 262 (M$^+$).

Example 3

4,7-Di-t-butyl-5-hydroxy-2-n-octyl-2,3-dihydrobenzofuran

1) Synthesis of 5-Benzyloxy-4-t-butyl-2-(1-octenyl)benzofuran

Under nitrogen atmosphere, 2.6 ml of n-butyl lithium (1.6 M in n-pentane) was added dropwise to a suspension of 1.84 g of n-heptylphenylphosphonium bromide in 10 ml of tetrahydrofuran. After stirring at room temperature for 30 minutes, a solution of 1.0 g of 5-benzyloxy-4-t-butyl-2-formylbenzofuran synthesized in Example 2-2) in 10 ml of tetrahydrofuran was added dropwise. Then, the mixture was heated under reflux for 30 minutes, cooled and then combined with a saturated aqueous ammonium chloride solution and extracted with chloroform. The organic layers were dried over anhydrous magnesium sulfate, then concentrated, and the residue was purified by silica gel column chromatography (in chloroform) to give 1.14 g of 5-benzyloxy-4-t-butyl-2-(1-octenyl)benzofuran as a colorless oil (yield 91%).

$^1$H NMR (60 MHz, CDCl$_3$) δ ppm: 0.89 (t, 3H, J=6.0 Hz), 1.13–1.72 (m, 8H), 1.56 (s, 9H), 1.93–2.62 (m, 2H), 5.03 (s, 2H), 6.02–6.40 (m, 2H), 6.78–7.46 (m, 8H).

Mass: 392 (M$^+$).

2) Synthesis of 4-t-Butyl-5-hydroxy-2-n-octylbenzofuran

Under hydrogen atmosphere, a solution of 1.1 g of 5-benzyloxy-4-t-butyl-2-(1-octenyl)benzofuran in 50 ml of acetic acid was stirred with 1.1 g of 10% palladium on carbon for 36 hours. After the palladium on carbon was filtered out, the filtrate was concentrated and the concentrate was purified by silica gel column chromatography (in chloroform) to give 0.6 g of 4-t-butyl-5-hydroxy-2-n-octylbenzofuran as a pale yellow oil (yield 69%).

$^1$H NMR (60 MHz, CDCl$_3$) δ ppm: 0.87 (t, 3H, J=6.0 Hz), 1.06–1.83 (m, 12H), 1.57 (s, 9H), 2.70 (t, 2H, J=7.0 Hz), 4.67 (s, 1H), 6.50 (d, 1H, J=8.4 Hz), 6.68 (s, 1H), 7.07 (d, 1H, J=8.4 Hz).

Mass: 302 (M$^+$).

3) Synthesis of 4-t-Butyl-5-hydroxy-2-n-octyl-2,3-dihydrobenzofuran 2.8 ml of triethylsilane was added to 0.3 g of 4-t-butyl-5-hydroxy-2-n-octylbenzofuran and then 1.4 ml of trifluoroacetic acid was added dropwise to this mixture under ice-cooling. After stirring at 0° C. for 15 minutes and then at room temperature for 1 hour, the mixture was poured into ice water and extracted with ethyl acetate. The extracted layers were washed with a saturated aqueous sodium bicarbonate solution, dried over anhydrous magnesium sulfate and then concentrated. The concentrate was purified by silica gel column chromatography (in chloroform) to give 0.25 g of 4-t-butyl-5-hydroxy-2-n-octyl-2,3-dihydrobenzofuran as a colorless oil (yield 83%).

$^1$H NMR (60 MHz, CDCl$_3$) δ ppm: 0.87 (t, 3H, J=6.0 Hz), 1.12–1.75 (m, 14H), 1.44 (s, 9H), 2.75–3.70 (m, 2H), 4.09–4.68 (m, 1H), 4.45 (s, 1H), 6.42 (s, 2H).

Mass: 304 (M$^+$).

4) Synthesis of 4,7-Di-t-butyl-5-hydroxy-2-n-octyl-2,3-dihydrobenzofuran

Under ice-cooling, 1.5 ml of methanesulfonic acid was added dropwise to a solution of 0.51 g of 4-t-butyl-5-hydroxy-2-n-octyl-2,3-dihydrobenzofuran in 0.85 g of t-butyl alcohol and 2 ml of chloroform. After stirring at 0° C. for 15 minutes, the mixture was poured into ice water and extracted with ethyl acetate. The extracted layers were washed with a saturated aqueous sodium bicarbonate solution, dried over anhydrous magnesium sulfate and then concentrated. The concentrate was purified by silica gel column chromatography (in n-hexane) to give 0.35 g of 4,7-di-t-butyl-5-hydroxy-2-n-octyl-2,3-dihydrobenzofuran as a pale yellow oil (yield 58%).

$^1$H NMR (200 MHz, CDCl$_3$) δ ppm: 0.87 (t, 3H, J=6.3 Hz), 1.22–1.37 (m, 12H), 1.30 (s, 9H), 1.45 (s, 9H), 1.52–1.62 (m, 2H), 2.92–3.08 (m, 1H), 3.38–3.56 (m, 1H), 4.36 (s, 1H), 4.49–4.64 (m, 1H), 6.41 (br, 1H).

Mass: 360 (M$^+$)

Example 4

4,7-Di-t-butyl-5-hydroxy-2,2-dimethyl-2,3-dihydrobenzofuran

1) Synthesis of 2,5-Di-t-butyl-4-trimethylacetoxyphenol

Under argon atmosphere, a solution of 11.12 g of 2,5-di-t-butylhydroquinone and 10.1 ml of anhydrous trimethylacetic acid in 200 ml of acetonitrile was stirred with a catalytic amount of sulfuric acid at room temperature for a whole day and night. After the reaction mixture was evaporated under reduced pressure, the concentrate was dissolved in diisopropyl ether. This solution was washed with a saturated aqueous sodium bicarbonate solution, then saturated brine, dried over anhydrous magnesium sulfate, and then concentrated. The concentrate was purified by silica gel column chromatography (in n-hexane containing 5% ethyl acetate) to give 11.9 g of 2,5-di-t-butyl-4-trimethylacetoxyphenol as a white solid (yield 78%).

$^1$H NMR (270 MHz, CDCl$_3$) δ ppm: 1.30 (s, 9H), 1.37 (s, 9H), 1.38 (s, 9H), 4.67 (s, 1H), 6.64 (s, 1H), 6.67 (s, 1H).

2) Synthesis of 2,5-Di-t-butyl-4-trimethylacetoxy-1-(2-methyl-2-propenyloxy)benzene Under a nitrogen stream, a solution of 0.50 g of 2,5-di-t-butyl-4-trimethylacetoxyphenol in 3 ml of dimethylformamide was added dropwise into a suspension of 0.08 g of oily sodium hydride in 3 ml of dimethylformamide. After stirring for 30 minutes, 0.19 ml of methallyl chloride was added dropwise and the mixture was stirred for 3 hours and allowed to attain room temperature. After the reaction was quenched with a saturated aqueous ammonium chloride solution, the mixture was extracted with water and n-hexane. The organic layers were washed with saturated brine, dried over anhydrous magnesium sulfate and then concentrated. The concentrate was purified by silica gel column chromatography (in n-hexane containing 1% ethyl acetate) to give 0.48 g of 2,5-di-t-butyl-4-trimethylacetoxy-1-(2-methyl-2-propenyloxy)benzene as a colorless oil (yield 82%).

$^1$H NMR (270 MHz, CDCl$_3$) δ ppm: 1.32 (s, 9H), 1.37 (s, 9H), 1.39 (s, 9H), 1.88 (s, 3H), 4.46 (s, 2H), 5.00 (d, 1H, J=1.7 Hz), 5.14 (d, 1H, J=1.7 Hz), 6.70 (s, 1H), 6.85 (s, 1H).

3) Synthesis of 4,7-Di-t-butyl-2,2-dimethyl-5-trimethylacetoxy-2,3-dihydrobenzofuran Under a nitrogen stream, a solution of 0.48 g of 2,5-di-t-butyl-4-trimethylacetoxy-1-(2-methyl-2-propenyloxy)benzene in 5 ml of dimethylaniline was refluxed overnight. The solution was allowed to attain room temperature and concentrated under reduced pressure, then extracted with ethyl acetate and 5% hydrochloric acid. The organic layers were washed with saturated brine, dried over anhydrous magnesium sulfate, and then concentrated. The concentrate was purified by silica gel column chromatography (in n-hexane containing 0.5% ethyl acetate) to give 0.43 g of 4,7-di-t-butyl-2,2-dimethyl-5-trimethylacetoxy-2,3-dihydrobenzofuran as a colorless solid.

4) Synthesis of 4,7-Di-t-butyl-5-hydroxy-2,2-dimethyl-2,3-dihydrobenzofuran

Under a nitrogen stream, 3.60 ml of diisobutylaluminium hydride (IM in n-hexane) was added dropwise into a solution of 0.43 g of 4,7-di-t-butyl-2,2-dimethyl-5-trimethylacetoxy-2,3-dihydrobenzofuran in 5 ml of n-hexane at room temperature, and the mixture was stirred overnight. After the reaction was quenched with 5% hydrochloric acid, the reaction solution was extracted with water and ethyl acetate. The organic layers were washed with saturated brine, dried over anhydrous magnesium sulfate and then concentrated. The concentrate was purified on a short column of silica gel (in n-hexane containing 0.2%–1% ethyl acetate) to give 0.22 g of 4,7-di-t-butyl-5-hydroxy-2,2-dimethyl-2,3-dihydrobenzofuran as a white solid (yield 67%).

$^1$H NMR (270 MHz, CDCl$_3$) δ ppm: 1.30 (s, 9H), 1.40 (s, 6H), 1.45 (s, 9H), 3.17 (s, 2H), 4.31 (s, 1H), 6.41 (s, 1H).

Mass: 276 (M$^+$)

Example 5

6-t-Butyl-5-hydroxy-2,2-dimethyl-2,3-dihydrobenzofuran

To 0.28 g of 4,6-di-t-butyl-5-hydroxy-2,2-dimethyl-2,3-dihydrobenzofuran synthesized according to JP 6-206842A/94 dissolved in 5 ml of chloroform was added 0.06 ml of methanesulfonic acid and the mixture was stirred at room temperature for 4 hours. Then, the reaction mixture was combined with a saturated aqueous sodium bicarbonate solution and extracted with chloroform. The extracted layers were washed with saturated brine, dried over anhydrous magnesium sulfate and then concentrated. The concentrate was purified by silica gel column chromatography (in n-hexane containing 10% ethyl acetate) to give 0.09 g of 6-t-butyl-5-hydroxy-2,2-dimethyl-2,3-dihydrobenzofuran as a white solid (yield 41%).

$^1$H NMR (270 MHz, CDCl$_3$) δ ppm: 1.37 (s, 9H), 1.45 (s, 6H), 2.93 (s, 2H), 4.53 (s, 1H), 6.51 (s, 1H), 6.69 (s, 1H).

Example 6

6-t-Butyl-5-hydroxy-2,2-di-n-pentyl-2,3-dihydrobenzofuran

To 1.03 g of 4,6-di-t-butyl-5-hydroxy-2,2-di-n-pentyl-2,3-dihydrobenzofuran synthesized according to JP No. 6-206842A/94 dissolved in 15 ml of dichloromethane was added 7 drops of methanesulfonic acid and the mixture was stirred at room temperature for a whole day and night. Then, the reaction mixture was combined with water and extracted with dichloromethane. The extracted layers were washed with saturated brine, dried over anhydrous magnesium sulfate and then concentrated. The concentrate was purified by silica gel column chromatography (in n-hexane containing 10% ethyl acetate) to give 0.19 g of 6-t-butyl-5-hydroxy-2,2-di-n-pentyl-2,3-dihydrobenzofuran as a colorless oil (yield 22%).

$^1$H NMR (270 MHz, CDCl$_3$) δ ppm: 0.88 (t, 6H, J=6.8 Hz), 1.10–1.42 (m, 12H), 1.37 (s, 9H), 1.58–1.75 (m, 4H), 2.90 (s, 2H), 4.32 (s, 1H), 6.48 (s, 1H), 6.67 (s, 1H).

$^1$H NMR (270 MHz, CDCl$_3$) δ ppm: 1.29 (s, 9H), 1.32 (s, 3H), 1.36 (s, 18H), 1.38 (s, 3H), 3.19 (s, 2H), 6.45 (s, 1H).

Mass: 332 (M$^+$).

Example 7

6-t-Butyl-5-hydroxy-2,3-dihydrobenzofuran-2-spiro-1'-cycloheptane

1) Synthesis of 4-Acetoxy-3-t-butylphenol

To 36 g of 3-t-butyl-4-hydroxyanisole dissolved in 100 ml of anhydrous acetic acid was added a catalytic amount of concentrated sulfuric acid and the mixture was stirred at room temperature for 6 days. After the reaction solution was concentrated under reduced pressure, the concentrate was dissolved in 200 ml of acetonitrile and combined with 60 g of sodium iodide. To the resulting solution was added dropwise 51 ml of trimethylsilyl chloride at room temperature and then the mixture was heated under reflux for 3 hours. The reaction mixture was allowed to attain room temperature, and then concentrated under reduced pressure, combined with water and extracted with ethyl acetate. The extracted layers were washed with saturated brine, then dried over anhydrous magnesium sulfate and concentrated to give 47.0 g of 4-acetoxy-3-t-butylphenol as a colorless oil (quantitative).

$^1$H NMR (60 MHz, CDCl$_3$) δ ppm: 1.30 (s, 9H), 2.29 (s, 3H), 5.50 (br, 1H), 6.30–7.15 (m, 3H).

2) Synthesis of 5-Acetoxy-4-t-butyl-2-hydroxybenzaldehyde

To 6.25 g of 4-acetoxy-3-t-butylphenol dissolved in 15 ml of trifluoroacetic acid was added 4.63 g of hexamethylenetetramine and the mixture was heated under reflux for 1 hour. The reaction mixture was allowed to attain room temperature, then poured into water and extracted with ethyl acetate. The organic layers were successively washed with a 1N aqueous sodium hydroxide solution, water and saturated brine, dried over anhydrous magnesium sulfate and concentrated. The concentrate was purified by silica gel column chromatography (in n-hexane containing 20% ethyl acetate) to give 3.68 g of 5-acetoxy-4-t-butyl-2-hydroxybenzaldehyde as a pale yellow oil (52%).

$^1$H NMR (270 MHz, CDCl$_3$) δ ppm: 1.35 (s, 9H), 2.35 (s, 3H), 7.02 (s, 1H), 7.22 (s, 1H), 9.80 (s, 1H), 10.78 (s, 1H)

Mass: 236 (M$^+$).

3) Synthesis of 4-Acetoxy-5-t-butyl-2-(cycloheptylhydroxymethyl)phenol and 5-t-Butyl-2-(cycloheptylhydroxymethyl)benzene-1,4-diol To 2.36 g of 5-acetoxy-4-t-butyl-2-hydroxybenzaldehyde dissolved in 10 ml of anhydrous tetrahydrofuran was added 0.40 g of oily sodium hydride under nitrogen atmosphere and the mixture was stirred at room temperature for 30 minutes. Then, 23 ml of a Grignard reagent (0.43 M in tetrahydrofuran) which has been prepared from magnesium and cycloheptyl bromide was added dropwise to this reaction mixture and the mixture was stirred at room temperature for 1 hour. Then, the mixture was combined with a saturated aqueous ammonium chloride solution and extracted with ethyl acetate. The organic layers were washed with saturated brine, then dried over anhydrous magnesium sulfate and then concentrated. The concentrate was purified by silica gel column chromatography (in n-hexane containing 15% ethyl acetate) to give 0.77 g of 4-acetoxy-5-t-butyl-2-(cycloheptylhydroxymethyl)phenol as a colorless oil (yield 23%) and 0.72 g of 5-t-butyl-2-(cycloheptylhydroxymethyl)benzene-1,4-diol as a colorless oil (yield 25%).

4-Acetoxy-5-t-butyl-2-(cycloheptylhydroxymethyl)phenol $^1$H NMR (270 MHz, CDCl$_3$) δ ppm: 1.20–2.00 (m, 13H), 1.31 (s, 9H), 2.30 (s, 3H), 4.53 (d, 1H, J=7.0 Hz), 6.54 (s, 1H), 6.85 (s, 1H).

5-t-Butyl-2-(cycloheptylhydroxymethyl)benzene-1,4-diol $^1$H NMR (270 MHz, CDCl$_3$) δ ppm: 1.17–2.00 (m, 13H), 1.38 (s, 9H), 3.84 (br, 1H), 4.49 (d, 1H, J=7.0 Hz), 6.27 (s, 1H), 6.78 (s, 1H).

4) Synthesis of 6-t-Butyl-5-hydroxy-2,3-dihydrobenzofuran-2-spiro-1'-cycloheptane To 0.66 g of 5-t-butyl-2-(cycloheptylhydroxymethyl)benzene-1,4-diol dissolved in 20 ml of chloroform was added 0.44 g of p-toluenesulfonic acid monohydrate and the mixture was stirred at room temperature for a whole day and night. After the reaction mixture was poured into water and extracted with chloroform, the organic layers were washed with saturated brine, dried over anhydrous magnesium sulfate and then concentrated. The concentrate was purified by silica gel column chromatography (in n-hexane containing 10% ethyl acetate) to give 0.27 g of 6-t-butyl-5-hydroxy-2,3-dihydrobenzofuran-2-spiro-1'-cycloheptane as a white solid (yield 43%).

$^1$H NMR (270 MHz, CDCl$_3$) δ ppm: 1.37 (s, 9H), 1.40–1.86 (m, 10H), 1.97–2.07 (m, 2H), 2.92 (s, 2H), 4.31 (s, 1H), 6.49 (s, 1H), 6.69 (s, 1H)

Mass: 274 (M$^+$).

Example 8

6-t-Butyl-5-hydroxy-4-(2-propenyl)-2,3-dihydrobenzofuran-2-spiro-1'-cycloheptane 1) Synthesis of 6-t-Butyl-5-(2-propenyloxy)-2,3-dihydrobenzofuran-2-spiro-1'-cycloheptane Under a nitrogen stream, a solution of 0.76 g of 6-t-butyl-5-hydroxy-2,3-dihydrobenzofuran-2-spiro-1'-cycloheptane synthesized in Example 7 in 6 ml of dimethylformamide was added dropwise to a suspension of 0.13 g of oily sodium hydride in 6 ml of dimethylformamide at 0° C. After stirring for 30 minutes, 0.28 ml of allyl bromide was added dropwise and the mixture was stirred overnight and allowed to attain room temperature. The reaction mixture was poured into a saturated aqueous ammonium chloride solution and extracted with n-hexane. The organic layers were washed with saturated brine, dried over anhydrous magnesium sulfate and then concentrated. The concentrate was purified by silica gel column chromatography (in n-hexane containing 1%–2% ethyl acetate) to give 0.76 g of 6-t-butyl-5-(2-propenyloxy)-2,3-dihydrobenzofuran-2-spiro-1'-cycloheptane as a colorless oil (yield 90%).

$^1$H NMR (270 MHz, CDCl$_3$) δ ppm: 1.18–2.06 (m, 12H), 1.36 (s, 9H), 2.96 (s, 2H), 4.47–4.50 (m, 2H), 5.22–5.28 (m, 1H), 5.39–5.47 (m, 1H), 6.02–6.16 (m, 1H), 6.70 (s, 1H), 6.72 (s, 1H).

Mass: 314 (M$^+$).

2) Synthesis of 6-t-Butyl-5-hydroxy-4-(2-propenyl)-2,3-dihydrobenzofuran-2-spiro-1'-cycloheptane Under a nitrogen stream, a solution of 0.76 g of 6-t-butyl-5-(2-propenyloxy)-2,3-dihydrobenzofuran-2-spiro-1'-cycloheptane was dissolved in 3 ml of dimethylaniline and the solution was refluxed overnight. The reaction mixture was allowed to attain room temperature and concentrated under reduced pressure, then extracted with ethyl acetate and 5% hydrochloric acid and the organic layers were washed with saturated brine, dried over anhydrous magnesium sulfate and then concentrated. The concentrate was purified by silica gel column chromatography (in n-hexane containing 1%–2% ethyl acetate) to give 0.51 g of 6-t-butyl-5-hydroxy-4-(2-propenyl)-2,3-dihydrobenzofuran-2-spiro-1'-cycloheptane as a colorless oil (yield 67%).

$^1$H NMR (270 MHz, CDCl$_3$) δ ppm: 1.24–2.05 (m, 12H), 1.35 (s, 9H), 2.89 (s, 2H), 3.28–3.31 (m, 2H), 4.58 (s, 1H), 5.10–5.17 (m, 2H), 5.88–6.00 (m, 1H), 6.61 (s, 1H).

Mass: 314 (M$^+$)

Example 9

6-t-Butyl-5-hydroxy-4-n-propyl-2,3-dihydrobenzofuran-2-spiro-1'-cycloheptane 0.51 g of 6-t-butyl-5-hydroxy-4-(2-propenyl)-2,3-dihydrobenzofuran-2-spiro-1'-cycloheptane synthesized in Example 8 was dissolved in 5 ml of ethanol and the solution was vigorously stirred with 0.05 g of 10% palladium on carbon overnight under a hydrogen stream. After the palladium on carbon was filtered off, the mixture was concentrated and the concentrate was purified by silica gel column chromatography (in n-hexane containing 1% ethyl acetate) to give 0.49 g of 6-t-butyl-5-hydroxy-4-n-propyl-2,3-dihydrobenzofuran-2-spiro-1'-cycloheptane as a white solid (yield 95%).

$^1$H NMR (270 MHz, CDCl$_3$) δ ppm: 1.02 (t, 3H, J=7.3 Hz), 1.28–2.09 (m, 14H), 1.41 (s, 9H), 2.50 (t, 2H, J=7.6 Hz), 2.93 (s, 2H), 4.35 (s, 1H), 6.61 (s, 1H).

Mass: 316 (M$^+$).

Example 10

6-t-Butyl-5-hydroxy-4-(2-methyl-2-propenyl)-2,3-dihydrobenzofuran-2-spiro-1'-cycloheptane 1) Synthesis of 6-t-Butyl-5-(2-methyl-2-propenyloxy)-2,3-dihydrobenzofuran-2-spiro-1'-cycloheptane 0.13 g of oily sodium hydride and 0.74 g of 6-t-butyl-5-hydroxy-2,3-dihydrobenzofuran-2-spiro-1'-cycloheptane synthesized in Example 7 were treated with 0.32 ml of methallyl chloride in dimethylformamide in the same manner as in Example 8-1) to give 0.89 g of 6-t-butyl-5-(2-methyl-2-propenyloxy)-2,3-dihydrobenzofuran-2-spiro-1'-cycloheptane as a colorless oil (quantitative).

$^1$H NMR (270 MHz, CDCl$_3$) δ ppm: 1.36 (s, 9H), 1.30–2.06 (m, 12H), 1.86 (s, 3H), 2.95 (s, 2H), 4.37 (s, 2H), 4.97 (s, 1H), 5.13 (s, 1H), 6.70 (s, 1H), 6.72 (s, 1H).

Mass: 328 (M$^+$)

2) Synthesis of 6-t-Butyl-5-hydroxy-4-(2-methyl-2-propenyl)-2,3-dihydrobenzofuran-2-spiro-1'-cycloheptane 0.89 g of 6-t-butyl-5-(2-methyl-2-propenyloxy)-2,3-dihydrobenzofuran-2-spiro-1'-cycloheptane was dissolved in 3 ml of dimethylaniline and the solution was treated in the same manner as in Example 8-2) to give 0.80 g of 6-t-butyl-5-hydroxy-4-(2-methyl-2-propenyl)-2,3-dihydrobenzofuran-2-spiro-1'-cycloheptane as a colorless oil (yield 90%).

$^1$H NMR (270 MHz, CDCl$_3$) δ ppm: 1.26–2.01 (m, 12H), 1.36 (s, 9H), 1.75 (s, 3H), 2.90 (s, 2H), 3.27 (s, 2H), 4.76 (s, 1H), 4.83 (s, 1H), 4.91 (s, 1H), 6.63 (s, 1H).

Mass: 328 (M$^+$).

Example 11

6-t-Butyl-5-hydroxy-4-(2-methylpropyl)-2,3-dihydrobenzofuran-2-spiro-1'-cycloheptane 0.80 g of 6-t-butyl-5-hydroxy-4-(2-methyl-2-propenyl)-2,3-dihydrobenzofuran-2-spiro-1'-cycloheptane synthesized in Example 10 was dissolved in 5 ml of ethanol and the solution was treated with 0.05 g of 10% palladium on carbon in the same manner as in Example 9 to give 0.56 g of 6-t-butyl-5-hydroxy-4-(2-methylpropyl)-2,3-dihydrobenzofuran-2-spiro-1'-cycloheptane as a pale yellow oil (yield 70%).

$^1$H NMR (270 MHz, CDCl$_3$) δ ppm: 0.96 (d, 6H, J=6.6 Hz), 1.26–2.01 (m, 13H), 1.38 (s, 9H), 2.37 (d, 2H, J=7.4 Hz), 2.90 (s, 2H), 4.31 (s, 1H), 6.59 (s, 1H).

Mass: 330 (M$^+$)

Example 12

6-t-Butyl-5-hydroxy-4-(1-methyl-2-propenyl)-2,3-dihydrobenzofuran-2-spiro-1'-cycloheptane 1) Synthesis of 5-(2-Butenyloxy)-6-t-butyl-2,3-dihydrobenzofuran-2-spiro-1'-cycloheptane 0.13 g of oily sodium hydride and 0.74 g of 6-t-butyl-5-hydroxy-2,3-dihydrobenzofuran-2-spiro-1'-cycloheptane synthesized in Example 7 were treated with 0.33 ml of crotyl bromide in dimethylformamide in the same manner as in Example 8-1) to give 0.82 g of a mixture of geometrical isomers of 5-(2-butenyloxy)-6-t-butyl-2,3-dihydrobenzofuran-2-spiro-1'-cycloheptane as a colorless oil (yield 93%).

$^1$H NMR (270 MHz, CDCl$_3$) δ ppm: 1.18–2.06 (m, 15H), 1.35 (s, 9H), 2.95 (s, 2H), 4.40 (d, J=4.3 Hz, 1.75H), 4.54 (d, J=5.6 Hz, 0.25H), 5.69–5.88 (m, 2H), 6.70–6.72 (m, 2H).

2) Synthesis of 6-t-Butyl-5-hydroxy-4-(1-methyl-2-propenyl)-2,3-dihydrobenzofuran-2-spiro-1'-cycloheptane 0.82 g of 5-(2-butenyloxy)-6-t-butyl-2,3-dihydrobenzofuran-2-spiro-1'-cycloheptane was dissolved in 3 ml of dimethylaniline and the solution was treated in the same manner as in Example 8-2) to give 0.14 g of 6-t-butyl-5-hydroxy-4-(1-methyl-2-propenyl)-2,3-dihydrobenzofuran-2-spiro-1'-cycloheptane as a white solid (yield 17%).

$^1$H NMR (270 MHz, CDCl$_3$) δ ppm: 1.31–2.07 (m, 12H), 1.35 (s, 9H), 1.41 (d. 3H, J=6.9 Hz), 2.94 (s, 2H), 3.53–3.57 m, 1H), 5.04 (s, 1H), 5.29–5.37 (m, 2H), 6.19–6.31 (m, 1H), 6.62 (s, 1H)

Mass: 328 (M$^+$).

Example 13

6-t-Butyl-5-hydroxy-4-(1-methylpropyl)-2,3-dihydrobenzofuran-2-spiro-1'-cycloheptane 0.07 g of 6-t-butyl-5-hydroxy-4-(1-methyl-2-propenyl)-2,3-dihydrobenzofuran-2-spiro-1'-cycloheptane synthesized in Example 12 was dissolved in 10 ml of ethanol and he solution was treated with 0.01 g of 10% palladium on carbon in the same manner as in Example 9 to give 0.05 g of 6-t-butyl-5-hydroxy-4-(1-methylpropyl)-2,3-dihydrobenzofuran-2-spiro-1'-cycloheptane as a pale yellow oil (yield 71%).

$^1$H NMR (270 MHz, CDCl$_3$) δ ppm: 0.88 (t, 3H, J=7.4 Hz), 1.22–2.17 (m, 14H), 1.27 (d, 3H, J=8.9 Hz), 1.38 (s, 9H), 2.80–2.89 (m, 1H), 2.97 (s, 2H), 4.34 (s, 1H), 6.58 (s, 1H).

Mass: 330 (M$^+$).

Example 14

6-t-Butyl-5-hydroxy-4-methyl-2,3-dihydrobenzofuran-2-spiro-1'-cycloheptane and 6-t-Butyl-4-ethyl-5-hydroxy-2,3-dihydrobenzofuran-2-spiro-1'-cycloheptane Under a nitrogen stream, 1.64 ml of diethylzinc (1M in n-hexane) was added dropwise into a solution of 0.18 ml of diiodomethane in 4 ml of anhydrous toluene at 0° C. Further to this solution was added dropwise 0.30 g of 6-t-butyl-5-hydroxy-2,3-dihydrobenzofuran-2-spiro-1'-cycloheptane synthesized in Example 7 and dissolved in 4 ml of anhydrous toluene. After stirring for 5 minutes, the solution was refluxed for 1.5 hours. The reaction solution was allowed to cool down, and then combined with a saturated aqueous sodium bicarbonate solution and extracted with ethyl acetate, and the organic layers were washed with saturated brine, dried over anhydrous magnesium sulfate and then concentrated. The concentrate was purified by silica gel column chromatography (in n-hexane containing 1%–2% ethyl acetate) to give 0.04 g of 6-t-butyl-5-hydroxy-4-methyl-2,3-dihydrobenzofuran-2-spiro-1'-cycloheptane (yield 13%) and 0.05 g of 6-t-butyl-4-ethyl-5-hydroxy-2,3-dihydrobenzofuran-2-spiro-1'-cycloheptane (yield 15%) both as white solids.

Example 14-(1)

6-t-Butyl-5-hydroxy-4-methyl-2,3-dihydrobenzofuran-2-spiro-1'-cycloheptane $^1$H NMR (270 MHz, CDCl$_3$) δ ppm: 1.22–1.98 (m, 12H), 1.38 (s, 9H), 2.11 (s, 3H), 2.91 (s, 2H), 4.25 (s, 1H), 6.58 (s, 1H).

Mass: 288 (M$^+$).

Example 14-(2)

6-t-Butyl-4-ethyl-5-hydroxy-2,3-dihydrobenzofuran-2-spiro-1'-cycloheptane $^1$H NMR (270 MHz, CDCl$_3$) δ ppm: 1.17 (t, 3H, J=7.6 Hz), 1.21–2.01 (m, 12H), 1.38 (s, 9H), 2.57 (q, 2H, J=7.6 Hz), 2.92 (s, 2H), 4.35 (s, 1H), 6.58 (s, 1H).

Mass: 302 (M$^+$)

Example 15

6-t-Butyl-5-hydroxy-2,3-dihydrobenzofuran

1) Synthesis of 3-t-Butyl-4-trimethylacetoxyanisole 5.00 g of 3-t-butyl-4-hydroxyanisole was dissolved in 30 ml of dimethylformamide and the solution was added dropwise into a suspension of 1.33 g of oily sodium hydride in 30 ml of dimethylformamide at 0° C. under a nitrogen stream. After stirring for 30 minutes, 3.76 ml of trimethylacetyl chloride was added dropwise and the solution was stirred overnight and allowed to attain room temperature. After the reaction was quenched with a saturated aqueous ammonium chloride solution, the reaction solution was extracted with water and ethyl acetate. The organic layers were washed with saturated brine, dried over anhydrous magnesium sulfate, and then concentrated. The concentrate was purified by silica gel column chromatography (in n-hexane containing 3%–5% ethyl acetate) to give 5.25 g of 3-t-butyl-4-trimethylacetoxyanisole as a white solid (yield 72%).

$^1$H NMR (270 MHz, CDCl$_3$) δ ppm: 1.33 (s, 9H), 1.38 (s, 9H), 3.79 (s, 3H), 6.69–6.80 (m, 2H), 6.92 (d, 1H, J=3.0 Hz).

Mass: 264 (M$^+$)

2) Synthesis of 3-t-Butyl-4-trimethylacetoxyphenol 5.00 g of 3-t-butyl-4-trimethylacetoxyanisole was dissolved in 45 ml of acetonitrile and 4.54 g of sodium iodide was added at room temperature under a nitrogen stream and 3.84 ml of trimethylsilyl chloride was further added dropwise. This solution was refluxed for 6 hours, then poured into a saturated aqueous sodium bicarbonate solution and extracted with diethyl ether. The organic layers were washed with saturated brine, dried over anhydrous magnesium sulfate and then concentrated. The concentrate was purified by silica gel column chromatography (in n-hexane containing 17% ethyl acetate) to give 4.50 g of 3-t-butyl-4-trimethylacetoxyphenol as a white solid (yield 95%).

$^1$H NMR (270 MHz, CDCl$_3$) δ ppm: 1.30 (s, 9H), 1.38 (s, 9H), 6.52–6.68 (m, 2H), 6.81 (d, 1H, J=3.0 Hz).

Mass: 250 (M$^+$).

3) Synthesis of 3-t-Butyl-1-(2,2-diethoxyethoxy)-4-trimethylacetoxybenzene 0.70 g of 3-t-butyl-4-trimethylacetoxyphenol was dissolved in 7 ml of dimethylformamide and the solution was added dropwise into a suspension of 0.13 g of oily sodium hydride in 7 ml of dimethylformamide at 0° C. under a nitrogen stream. After stirring for 30 minutes, 0.50 ml of bromoacetaldehyde diethylacetal was added dropwise and the solution was stirred overnight and allowed to attain room temperature. After the reaction was quenched with a saturated aqueous ammonium chloride solution, the reaction mixture was extracted with water and ethyl acetate and the organic layers were washed with saturated brine, dried over anhydrous magnesium sulfate and then concentrated. The concentrate was purified by silica gel column chromatography (in n-hexane containing 1% –5% ethyl acetate) to give 0.21 g of 3-t-butyl-1-(2,2-diethoxyethoxy)-4-trimethylacetoxybenzene as a white solid (yield 21%).

$^1$H NMR (270 MHz, CDCl$_3$) δ ppm: 1.25 (t, 6H, J=6.9 Hz), 1.32 (s, 9H), 1.38 (s, 9H), 3.58–3.82 (m, 4H), 3.99 (d, 2H, J=5.3 Hz), 4.83 (t, 1H, J=5.1 Hz), 6.70–6.78 (m, 2H), 6.95 (d, 1H, J=2.6 Hz)

4) Synthesis of 6-t-Butyl-5-trimethylacetoxybenzofuran 0.20 g of 3-t-butyl-1-(2,2-diethoxyethoxy)-4-trimethylacetoxybenzene was dissolved in 10 ml of benzene and 0.20 g of polyphosphoric acid was added. The mixture was refluxed for one hour. After the solution was allowed to cool down, polyphosphoric acid was decanted off and the organic layers were concentrated. The concentrate was purified by silica gel column chromatography (in n-hexane containing 5% ethyl acetate) to give 0.13 g of 6-t-butyl-5-trimethylacetoxybenzofuran as a pale yellow liquid (yield 87%).

$^1$H NMR (270 MHz, CDCl$_3$) δ ppm: 1.42 (s, 9H), 1.45 (s, 9H), 6.69–6.70 (m, 1H), 7.10 (s, 1H), 7.55 (d, 1H, J=0.7 Hz), 7.61 (d, 1H, J=2.0 Hz).

5) Synthesis of 6-t-Butyl-5-hydroxybenzofuran

Under a nitrogen stream, 0.12 g of 6-t-butyl-5-trimethylacetoxybenzofuran was dissolved in 5 ml of n-hexane at room temperature and 1.31 ml of diisobutylaluminium hydride (1M in n-hexane) was added dropwise and the mixture was stirred overnight. After the reaction was quenched with 5% hydrochloric acid, the mixture was extracted with water and ethyl acetate. The organic layers were washed with saturated brine, dried over anhydrous magnesium sulfate and then concentrated. The concentrate was purified on a short column of silica gel (in n-hexane containing 5% ethyl acetate) to give 0.07 g of 6-L-butyl-5-hydroxybenzofuran as a reddish brown oil.

$^1$H NMR (270 MHz, CDCl$_3$) δ ppm: 1.46 (s, 9H), 4.72 (s, 1H), 6.60–6.61 (m, 1H), 6.84 (s, 1H), 7.43 (s, 1H), 7.53 (d, 1H, J=2.3 Hz).

Mass: 190 (M$^+$)

6) Synthesis of 6-t-Butyl-5-hydroxy-2,3-dihydrobenzofuran 0.07 g of 6-t-butyl-5-hydroxybenzofuran was dissolved in 5 ml of acetic acid and a catalytic amount of 10% palladium on carbon was added. The mixture was stirred under a hydrogen pressure (3.5 kg/cm$^2$) for 6 hours. After the palladium on carbon was filtered off, the solution was concentrated and the concentrate was purified by silica gel column chromatography (in n-hexane containing 9% ethyl acetate) to give 0.05 g of 6-t-butyl-5-hydroxy-2,3-dihydrobenzofuran as a white solid (yield 71%).

$^1$H NMR (270 MHz, CDCl$_3$) δ ppm: 1.38 (s, 9H), 3.13 (t, 2H, J=8.6 Hz), 4.44 (s, 1H), 4.51 (t, 2H, J=8.6 Hz), 6.57 (s, 1H), 6.75 (s, 1H).

Mass: 193 (M$^+$+1).

Example 16

6-t-Butyl-5-hydroxy-2-methyl-2,3-dihydrobenzofuran

1) Synthesis of 3-t-Butyl-4-trimehtylacetoxy-1-(2-propenyloxy)benzene

Under a nitrogen stream, 4.48 g of 3-t-butyl-4-trimethylacetoxyphenol synthesized in Example 15-2) was dissolved in 20 ml of dimethylformamide and a suspension of 0.86 g of oily sodium hydride in 20 ml of dimethylformamide at 0° C. was added dropwise. After stirring for 30 minutes, 1.86 ml of allyl bromide was added dropwise and the solution was stirred for 3 hours and allowed to attain room temperature. After the reaction was quenched with a saturated aqueous ammonium chloride solution, the mixture was extracted with water and n-hexane. The organic layers were washed with saturated brine, dried over anhydrous magnesium sulfate and then concentrated. The concentrate was purified by silica gel column chromatography (in n-hexane containing 1% ethyl acetate) to give 4.31 g of 3-t-butyl-4-trimethylacetoxy-1-(2-propenyloxy)benzene as a colorless oil (yield 83%).

$^1$H NMR (270 MHz, CDCl$_3$) δ ppm: 1.32 (s, 9H), 1.38 (s, 9H), 4.49–4.52 (m, 2H), 5.26–5.45 (m, 2H), 5.98–6.13 (m, 1H), 6.71–6.79 (m, 2H), 6.95 (d, J=3.3 Hz, 1H).

2) Synthesis of 5-t-Butyl-4-trimethylacetoxy-2-(2-propenyl)phenol 4.30 g of 3-t-butyl-4-trimethylacetoxy-1-(2-propenyloxy) benzene was dissolved in 30 ml of dimethylaniline and the solution was refluxed overnight under a nitrogen stream. The solution was allowed to attain room temperature and concentrated under reduced pressure, then extracted with ethyl acetate and 5% hydrochloric acid and the organic layers were washed with saturated brine, dried over anhydrous magnesium sulfate and then concentrated. The concentrate was purified by silica gel column chromatography (in n-hexane containing 0.5% ethyl acetate) to give 1.70 g of 5-t-butyl-4-trimethylacetoxy-2-(2-propenyl)phenol as a colorless solid.

$^1$H NMR (270 MHz, CDCl$_3$) δ ppm: 1.30 (s, 9H), 1.38 (s, 9H), 3.32 (s, 2H), 4.88–5.22 (m, 3H), 5.93–6.03 (m, 1H), 6.59 (s, 1H), 6.82 (s, 1H)

Mass: 314 (M$^+$).

3) Synthesis of 6-t-Butyl-2-methyl-5-trimethylacetoxy-2,3-dihydrobenzofuran 0.50 g of 5-t-butyl-4-trimethylacetoxy-2-(2-propenyl) phenol was dissolved in 30 ml of dichloromethane, 30 ml of boron trifluoride etherate was added, and the solution was stirred at room temperature under a nitrogen stream. The solution was further refluxed for 30 minutes, and the reaction solution was poured into a saturated aqueous sodium bicarbonate solution and extracted with n-hexane. The organic layers were washed with saturated brine, dried over anhydrous magnesium sulfate and then concentrated. The concentrate was purified by silica gel column chromatography (in n-hexane containing 0.5%–1% ethyl acetate) to give 0.15 g of 6-t-butyl-2-mehtyl-5-trimethylacetoxy-2,3-dihydrobenzofuran as a colorless solid (yield 30%).

$^1$H NMR (270 MHz, CDCl$_3$) δ ppm: 1.30 (s, 9H), 1.38 (s, 9H), 1.45 (d, 3H, J=6.3 Hz), 2.73–2.81 (m, 1H), 3.21–3.30 (m, 1H), 4.87–4.93 (m, 1H), 6.65 (s, 1H), 6.78 (s, 1H).

4) Synthesis of 6-t-Butyl-5-hydroxy-2-methyl-2,3-dihydrobenzofuran

Under a nitrogen stream, 0.15 g of 6-t-butyl-2-methy-5-trimethylacetoxy-2,3-dihydrobenzofuran was dissolved in 3 ml of n-hexane at room temperature, 1.55 ml of diisobutylaluminium hydride (1M in n-hexane) was added dropwise, and the mixture was stirred overnight. After the reaction was quenched with 5% hydrochloric acid, the mixture was extracted with water and ethyl acetate. The organic layers were washed with saturated brine, dried over anhydrous magnesium sulfate and then concentrated. The concentrate was purified on a short column of silica gel (in n-hexane containing 5% ethyl acetate) to give 0.09 g of 6-t-butyl-5-hydroxy-2-methyl-2,3-dihydrobenzofuran as a white solid (yield 84%).

$^1$H NMR (270 MHz, CDCl$_3$) δ ppm: 1.38 (s, 9H), 1.45 (d, 3H, J=6.3 Hz), 2.68–2.80 (m, 1H), 3.21–3.30 (m, 1H), 4.40 (s, 1H), 4.80–4.93 (m, 1H), 6.53 (s, 1H), 6.72 (s, 1H).

Mass: 206 (M$^+$)

Example 17

2,2-Diethyl-5-hydroxy-4,6-diisopropyl-2,3-dihydrobenzofuran

1) Synthesis of 5-Acetoxy-2-hydroxy-4,6-diisopropylbenzaldehyde 1.00 g of 4-acetoxy-3,5-diisopropylphenol and 0.71 g of hexamethylenetetramine were dissolved in 4 ml of trifluoroacetic acid and the mixture was heated under reflux for 20 minutes. The reaction solution was cooled to 0° C., then combined with water and extracted with ethyl acetate. The organic layers were washed with a saturated aqueous sodium bicarbonate solution and then saturated brine, dried over anhydrous magnesium sulfate and then concentrated. The concentrate was dissolved in 10 ml of methanol, 13 ml of 1N hydrochloric acid was added, and the solution was heated under reflux for 1.5 hours. The reaction mixture was cooled to room temperature, then combined with water and extracted with ethyl acetate. The organic layers were washed with saturated brine, dried over anhydrous magnesium sulfate and then concentrated. The concentrate was purified by silica gel column chromatography (in n-hexane containing 5%–10% ethyl acetate) to give 0.78 g of 5-acetoxy-2-hydroxy-4,6-diisopropylbenzaldehyde as a pale yellow oil (yield 70%).

$^1$H NMR (270 MHz, CDCl$_3$) δ ppm: 1.19 (d, 6H, J=6.9 Hz), 1.40 (d, 3H, J=6.9 Hz), 1.43 (d, 3H, J=6.9 Hz), 2.35 (s, 3H), 2.82 (septet, 1H J=6.9 Hz), 3.46 (septet, 1H, J=6.9 Hz), 6.80 (s, 1H), 10.47 (s, 1H), 12.21 (s, 1H).

2) Synthesis of 4-Acetoxy-2-(2-ethyl-1-hydroxybutyl)-3,5-diisopropylphenol

Under argon atmosphere, 0.78 g of 5-acetoxy-2-hydroxy-4,6-diisopropylbenzaldehyde was dissolved in 2 ml of anhydrous tetrahydrofuran and a solution of 0.40 g of oily sodium hydride in 1 ml of anhydrous tetrahydrofuran was added. After additional 5 ml of anhydrous tetrahydrofuran was added, the solution was stirred at room temperature for 30 minutes. Then, 5 ml of a Grignard reagent (1.48M in tetrahydrofuran) prepared from magnesium and 3-bromopentane was added dropwise to this reaction solution and the mixture was stirred at room temperature for 2 hours. Then, the mixture was combined with water and 1M hydrochloric acid and extracted with ethyl acetate. The organic layers were washed with saturated brine, then dried over anhydrous magnesium sulfate, and then concentrated. The concentrate was purified by silica gel column chromatography (in n-hexane containing 10% ethyl acetate) to give 0.51 g of 4-acetoxy-2-(2-ethyl-1-hydroxybutyl)-3,5-diisopropylphenol as a white amorphous material (yield 51%).

Mass: 336 (M$^+$).

3) Synthesis of 5-Acetoxy-2,2-diethyl-4,6-diisopropyl-2,3-dihydrobenzofuran 0.51 g of 4-acetoxy-2-(2-ethyl-1-hydroxybutyl)-3,5-diisopropylphenol dissolved in 10 ml of toluene, 0.58 g of p-toluenesulfonic acid monohydrate was added, and the mixture was heated under reflux for 1.5 hours. The reaction mixture was combined with a 2N aqueous sodium hydroxide solution and extracted with hexane. The organic layers were washed with saturated brine, dried over anhydrous magnesium sulfate and then concentrated. The concentrate was purified by silica gel column chromatography (in n-hexane containing 1% ethyl acetate) to give 433 mg of 5-acetoxy-2,2-diethyl-4,6-diisopropyl-2,3-dihydrobenzofuran as a yellow oil (yield 90%).

$^1$H NMR (270 MHz, CDCl$_3$) δ ppm: 0.93 (t, 6H, J=7.3 Hz), 1.15 (d, 6H, J=6.9 Hz), 1.21 (d, 6H, J=6.9 Hz), 1.63–1.82 (m, 4H), 2.32 (s, 3H), 2.79 (septet, 1H, J=6.9 Hz), 2.96 (septet, 1H, J=6.9 Hz), 3.00 (s, 2H), 6.54 (s, 1H).

Mass: 318 (M$^+$).

4) Synthesis of 2,2-Diethyl-5-hydroxy-4,6-diisopropyl-2,3-dihydrobenzofuran

Under argon atmosphere, 432 mg of 5-acetoxy-2,2-diethyl-4,6-diisopropyl-2,3-dihydrobenzofuran was dissolved in 3 ml of anhydrous tetrahydrofuran, a solution of 129 mg of lithium aluminium hydride in 2 ml of anhydrous tetrahydrofuran was added, and the solution was stirred at room temperature for 6 hours. After the reaction was quenched with water, the reaction solution was combined with 10% hydrochloric acid and extracted with ethyl acetate. The organic layers were washed with saturated brine, dried over anhydrous magnesium sulfate and then concentrated. The concentrate was purified by silica gel column chromatography (in n-hexane containing 1% ethyl acetate) to give 376 mg of 2,2-diethyl-5-hydroxy-4,6-diisopropyl-2,3-dihydrobenzofuran as a light brown solid (yield 100%).

$^1$H NMR (270 MHz, CDCl$_3$) δ ppm: 0.92 (t, 6H, J=7.3 Hz), 1.22 (d, 6H, J=6.9 Hz), 1.31 (d, 6H, J=6.9 Hz), 1.64–1.79 (m, 4H), 2.97 (s, 2H), 3.04 (septet, 1H, J=6.9 Hz), 3.22 (septet, 1H, J=6.9 Hz), 4.20 (s, 1H), 6.47 (s, 1H).

Mass: 276 (M$^+$).

Example 18

5-Hydroxy-2,2-dimethyl-4,6-diisopropyl-2,3-dihydrobenzofuran

1) Synthesis of 5-Acetoxy-2,2-dimethyl-4,6-diisopropyl-2,3-dihydrobenzofuran

Under argon atmosphere, 294 mg of 4-acetoxy-3,5-diisopropylphenol was dissolved in 10 ml of anhydrous dichloromethane, 2.25 g of 3-chloro-2-methyl-1-propene, 202 mg of anhydrous zinc chloride and 0.5 ml of acetic acid were added, and the mixture was stirred at room temperature for 3 days. After the reaction was quenched with water, the reaction solution was extracted with hexane. The organic layers were washed with a saturated aqueous sodium bicarbonate solution and saturated brine, dried over anhydrous magnesium sulfate and then concentrated. The concentrate was purified by silica gel column chromatography (in n-hexane containing 1% ethyl acetate) to give 316 mg of 5-acetoxy-2,2-dimethyl-4,6-diisopropyl-2,3-dihydrobenzofuran as a yellow oil (yield 88%).

$^1$H NMR (300 MHz, CDCl$_3$) δ ppm: 1.15 (d, 6H, J=6.9 Hz), 1.21 (d, 6H, J=6.9 Hz), 1.46 (s, 6H), 2.33 (s, 3H), 2.80 (septet, 1H, J=6.9 Hz), 2.96 (septet, 1H, J=6.9 Hz), 3.06 (s, 2H), 6.55 (s, 1H).

Mass: 290 (M$^+$)

2) Synthesis of 5-Hydroxy-2,2-dimethyl-4,6-diisopropyl-2,3-dihydrobenzofuran

Under argon atmosphere, 77 mg of 5-acetoxy-2,2-dimethyl-4,6-diisopropyl-2,3-dihydrobenzofuran was dissolved in 1 ml of anhydrous tetrahydrofuran, a solution of 25 mg of lithium aluminium hydride in 2 ml of anhydrous tetrahydrofuran was added, and the solution was stirred at room temperature for a whole day and night. After cooling to 0° C., the reaction was quenched with water and then the reaction mixture was extracted with a 10% aqueous hydrochloric acid solution and ethyl acetate. The organic layers were washed with saturated brine, dried over anhydrous magnesium sulfate and then concentrated. The concentrate was purified by silica gel column chromatography (in n-hexane containing 1% ethyl acetate) to give 42 mg of 5-hydroxy-2,2-dimethyl-4,6-diisopropyl-2,3-dihydrobenzofuran as a light red solid (yield 64%).

$^1$H NMR (270 MHz, CDCl$_3$) δ ppm: 1.22 (d, 6H, J=6.9 Hz), 1.31 (d, 6H, J=6.9 Hz), 1.45 (s, 6H), 3.02 (s, 2H), 3.05 (septet, 1H, J=6.9 Hz), 3.21 (septet, 1H, J=6.9 Hz), 4.24 (s, 1H), 6.47 (s, 1H).

Mass: 248 (M$^+$).

Example 19

6-t-Butyl-5-hydroxy-2,2,4-trimethyl-2,3-dihydrobenzofuran

1) Synthesis of 1,4-Diacetoxy-2-t-butyl-6-methylbenzene

To 100 ml of methanol was added dropwise 3.5 ml of concentrated sulfuric acid followed by a solution of 10.0 g of 2-t-butyl-6-methylphenol and 11.5 g of 47% hydrobromic acid in 60 ml of methanol. While the reaction mixture was heated with stirring, 17.3 g of 30% aqueous hydrogen peroxide was added dropwise and the mixture was heated with stirring for 30 minutes. After cooling to room temperature, the reaction mixture was extracted with hexane. The organic layers were washed with a 2N aqueous sodium hydroxide solution, a saturated aqueous sodium thiosulfate solution and saturated brine, then dried over anhydrous magnesium sulfate, and then concentrated. 14.6 g of the concentrate was dissolved in 150 ml of acetic anhydride, 2.68 g of zinc was added, and the mixture was heated with stirring for one hour. After cooling to 0° C., 15 ml of concentrated sulfuric acid was added dropwise, and then the solution was allowed to attain room temperature and stirred for one hour. After zinc was removed from the reaction mixture and the reaction was quenched with water, the reaction solution was extracted with ethyl acetate. The organic layers were washed with a saturated aqueous sodium bicarbonate solution and saturated brine, then dried over anhydrous magnesium sulfate and then concentrated. The concentrate was purified by silica gel column chromatography (in n-hexane containing 5%–10% ethyl acetate) to give 4.66 g of 1,4-diacetoxy-2-t-butyl-6-methylbenzene as a yellow oil (29%).

$^1$H NMR (270 MHz, CDCl$_3$) δ ppm: 1.32 (s, 9H), 2.10 (s, 3H), 2.28 (s, 3H), 2.34 (s, 3H), 6.85 (d, 1H, J=2.6 Hz), 6.92 (d, 1H, J=2.6 Hz)

2) Synthesis of 4-Acetoxy-3-t-butyl-5-methylphenol 1.05 g of 1,4-diacetoxy-2-t-butyl-6-methylbenzene was dissolved in 10 ml of ethanol and 2 ml of an aqueous solution containing 0.23 g of sodium hydrosulfite and 0.17 g of sodium hydroxide was added dropwise with stirring at 0° C. The reaction solution was neutralized with 1N hydrochloric acid, and then combined with water and extracted with ethyl acetate. The organic layers were dried over anhydrous magnesium sulfate, and then concentrated. The concentrate was purified by silica gel column chromatography (in n-hexane containing 10% ethyl acetate) to give 0.44 g of 4-acetoxy-3-t-butyl-5-methylphenol as a pale yellow oil (yield 50%).

$^1$H NMR (270 MHz, CDCl$_3$) δ ppm: 1.31 (s, 9H), 2.06 (s, 3H), 2.33 (s, 3H), 4.65 (s, 1H), 6.53 (d, 1H, J=2.6 Hz), 6.69 (d, 1H, J=2.6 Hz)

3) Synthesis of 5-Acetoxy-4-t-butyl-2-hydroxy-6-methylbenzaldehyde 0.33 g of 4-acetoxy-3-t-butyl-5-methylphenol and 0.33 g of hexamethylenetetramine were dissolved in 2 ml of trifluoroacetic acid and the solution was heated under reflux for 15 minutes. After cooling to 0° C., the reaction solution was combined with water, neutralized with a 2N aqueous sodium hydroxide solution, and then extracted with ethyl acetate. The organic layers were washed with a saturated aqueous ammonium chloride solution and saturated brine, dried over anhydrous magnesium sulfate and then concentrated. The concentrate was dissolved in 5 ml of methanol and heated with 3.9 ml of 1N hydrochloric acid under reflux for one hour. The reaction solution was returned to room temperature and then combined with water, and the precipitated crystal was filtered off. After drying, 0.35 g of 5-acetoxy-4-t-butyl-2-hydroxy-6-methylbenzaldehyde was obtained as a white solid (72%).

$^1$H NMR (270 MHz, CDCl$_3$) δ ppm: 1.33 (s, 9H), 2.31 (s, 3H), 2.37 (s, 3H), 6.88 (s, 1H), 10.27 (s, 1H), 11.84 (s, 1H).

4) Synthesis of 4-Acetoxy-5-t-butyl-2-(1-hydroxy-2-methylpropyl)-3-methylphenol

Under argon atmosphere, 5-acetoxy-4-t-butyl-2-hydroxy-6-methylbenzaldehyde was dissolved in 10 ml of anhydrous tetrahydrofuran, 10 ml of isopropylmagnesium bromide (0.76M in tetrahydrofuran) was added dropwise and the mixture was stirred at room temperature for 30 minutes. After the reaction was quenched with distilled water, the reaction mixture was combined with 1N hydrochloric acid and extracted with ethyl acetate. The organic layers were washed with saturated brine, then dried over anhydrous magnesium sulfate, and then concentrated to give 0.44 g of 4-acetoxy-5-t-butyl-2-(1-hydroxy-2-methylpropyl)-3-methylphenol as a yellow amorphous material (yield 100%).

Mass: 294 (M$^+$).

5) Synthesis of 5-Acetoxy-6-t-butyl-2,2,4-trimethyl-2,3-dihydrobenzofuran 0.40 g of 4-acetoxy-5-t-butyl-2-(1-hydroxy-2-methylpropyl)-3-methylphenol was dissolved in 10 ml of anhydrous toluene, 0.35 ml of boron trifluoride ethyl ether was added dropwise, and the mixture was stirred at room temperature for a whole day and night. After the reaction was quenched with water, the mixture was extracted with ethyl acetate. The organic layers were washed with a saturated aqueous sodium bicarbonate solution and saturated brine, dried over anhydrous magnesium sulfate and then concentrated. The concentrate was purified by silica gel column chromatography (in n-hexane containing 1%–2% ethyl acetate) to give 70 mg of 5-acetoxy-6-t-butyl-2,2,4-trimethyl-2,3-dihydrobenzofuran as a pale yellow oil (yield 19%).

$^1$H NMR (270 MHz, CDCl$_3$) δ ppm: 1.30 (s, 9H), 1.47 (s, 6H), 1.95 (s, 3H), 2.33 (s, 3H), 2.92 (s, 2H), 6.64 (s, 1H).

Mass: 276 (M$^+$).

6) Synthesis of 6-t-Butyl-5-hydroxy-2,2,4-trimethyl-2,3-dihydrobenzofuran

Under argon atmosphere, 65 mg of 5-acetoxy-6-t-butyl-2,2,4-trimethyl-2,3-dihydrobenzofuran was dissolved in 1.5 ml of anhydrous tetrahydrofuran, a solution of 22 mg of lithium aluminium hydride in 1 ml of anhydrous tetrahydrofuran was added, and the mixture was stirred at room temperature for a whole day and night. After cooling to 0° C, the reaction was quenched with water and then the reaction solution was combined with 10% hydrochloric acid and extracted with ethyl acetate. The organic layers were washed with a saturated aqueous sodium bicarbonate solution and saturated brine, dried over anhydrous magnesium sulfate, and then concentrated. The concentrate was recrystallized from hexane to give 25 mg of 6-t-butyl-5-hydroxy-2,2,4-trimethyl-2,3-dihydrobenzofuran as a white solid (yield 45%).

$^1$H NMR (270 MHz, CDCl$_3$) δ ppm: 1.38 (s, 9H), 1.46 (s, 6H), 2.11 (s, 3H), 2.92 (s, 2H), 4.31 (s, 1H), 6.59 (s, 1H).

Mass: 234 (M$^+$).

Example 20

6-t-Butyl-5-hydroxy-2,2-dimethyl-4-isopropyl-2,3-dihydrobenzofuran and 4-t-Butyl-5-hydroxy-2,2-dimethyl-6-isopropyl-2,3-dihydrobenzofuran 1) Synthesis of 1,4-Diacetoxy-2-t-butyl-6-isopropylbenzene To 100 ml of methanol was added dropwise 4 ml of concentrated sulfuric acid followed by a solution of 17.18 g of 2,4-di-t-butyl-6-isopropylphenol and 12.8 g of 47% hydrobromic acid in 66 ml of methanol. While the reaction solution was heated with stirring, 19.6 g of 30% aqueous hydrogen peroxide was added dropwise and the mixture was heated with stirring for 15 minutes. After cooling to room temperature, the reaction mixture was combined with distilled water and extracted with hexane. The organic layers were washed with a 0.5N aqueous sodium hydroxide solution and a saturated aqueous sodium thiosulfate solution, then dried over anhydrous magnesium sulfate, and then concentrated. 14.6 g of the concentrate was dissolved in 70 ml of hexane, a solution of 36.1 g of sodium hydrosulfite in 210 ml of distilled water was added, followed by 140 ml of methanol, and the mixture was stirred at room temperature for 30 minutes. The reaction solution was combined with water and extracted with a mixture of hexane and ethyl acetate. The organic layers were washed with saturated brine, then dried over anhydrous magnesium sulfate, and then concentrated. The concentrate was dissolved in 35 ml of acetic anhydride, and the solution was stirred with 0.35 ml of concentrated sulfuric acid at room temperature for 30 minutes. After cooling to 0° C., the reaction was quenched with water, and the reaction solution was combined with saturated brine and extracted with a mixture of hexane and ethyl acetate. The organic layers were washed with a 0.5 N aqueous sodium hydroxide solution and saturated brine, then dried over anhydrous magnesium sulfate, and then concentrated. The concentrate was purified by silica gel column chromatography (in n-hexane containing 10% ethyl acetate) to give 15.07 g of 1,4-diacetoxy-2-t-butyl-6-isopropylbenzene as a yellow solid (yield 74%).

$^1$H NMR (270 MHz, CDCl$_3$) δ ppm: 1.14 (d, 3H, J=6.9 Hz), 1.20 (d, 3H, J=6.9 Hz), 1.32 (s, 9H), 2.29 (s, 3H), 2.35 (s, 3H), 2.75 (qq, 1H, J=6.9 Hz, J=6.9 Hz), 6.92 (d, 1H, J=2.6 Hz), 6.94 (d, 1H, J=2.6 Hz).

2) Synthesis of 4-Acetoxy-3-t-butyl-5-isopropylphenol 1.10 g of 1,4-diacetoxy-2-t-butyl-6-isopropylbenzene was dissolved in 22 ml of methanol, 2.5 ml of 3N hydrochloric acid was added, and the solution was heated under reflux for 2.5 hours. After cooling to room temperature, methanol was distilled off on a rotary evaporator. The concentrate was combined with water and extracted with ethyl acetate. The organic layers were washed with saturated brine, dried over anhydrous magnesium sulfate, and then concentrated. The concentrate was purified by silica gel column chromatography (in n-hexane containing 5%–10% ethyl acetate) to give 0.66 g of 4-acetoxy-3-t-butyl-5-isopropylphenol as a pale yellow solid (yield 70%).

$^1$H NMR (270 MHz, CDCl$_3$) δ ppm: 1.13 (d, 3H, J=6.9 Hz), 1.20 (d, 3H, J=6.9 Hz), 1.31 (s, 9H), 2.34 (s, 3H), 2.72 (qq, 1H, J=6.9 Hz, J=6.9 Hz), 4.60 (s, 1H), 6.65 (d, 1H, J=3.0 Hz), 6.71 (d, 1H, J=3.0 Hz).

3) Synthesis of 5-Acetoxy-4-t-butyl-2-hydroxy-6-isopropylbenzaldehyde and 5-Acetoxy-6-t-butyl-2-hydroxy-4-isopropylbenzaldehyde 0.75 g of 4-acetoxy-3-t-butyl-5-isopropylphenol and hexamethylenetetramine were dissolved in 2.6 ml of trifluoroacetic acid and the solution was heated under reflux for 15 minutes. After cooling to 0° C., 2 ml of 3N hydrochloric acid was added and the solution was heated under reflux for 1.5 hours. Additional 2 ml of 3N hydrochloric acid was added and the solution was heated under reflux for 5 hours. After cooling to room temperature, the reaction solution was combined with water and extracted with ethyl acetate. The organic layers were washed with saturated brine, dried over anhydrous magnesium sulfate, and then concentrated. The concentrate was purified by silica gel column chromatography (in n-hexane containing 5% ethyl acetate) to give 0.40 g of a mixture of 5-acetoxy-4-t-butyl-2-hydroxy-6-isopropylbenzaldehyde and 5-acetoxy-6-t-butyl-2-hydroxy-4-isopropylbenzaldehyde as a pale yellow oil (yield 48%).

5-Acetoxy-4-t-butyl-2-hydroxy-6-isopropylbenzaldehyde $^1$H NMR (270 MHz, CDCl$_3$) δ ppm: 1.32 (s, 9H), 1.41 (d, 3H, J=7.3 Hz), 1.46 (d, 3H, J=7.3 Hz), 2.36 (s, 3H), 3.20 (qq, 1H, J=7.3 Hz, J=7.3 Hz), 6.91 (s, 1H), 10.55 (s, 1H), 12.17 (s, 1H).

5-Acetoxy-6-t-butyl-2-hydroxy-4-isopropylbenzaldehyde $^1$H NMR (270 MHz, CDCl$_3$) δ ppm: 1.32 (s, 9H), 1.41 (d, 3H, J=7.3 Hz), 1.46 (d, 3H, J=7.3 Hz), 2.36 (s, 3H), 3.20 (qq, 1H, J=7.3 Hz, J=7.3 Hz), 6.91 (s, 1H), 10.55 (s, 1H), 12.17 (s, 1H).

4) Synthesis of 6-t-Butyl-5-hydroxy-2,2-dimethyl-4-isopropyl-2,3-dihydrobenzofuran and 4-t-Butyl-5-hydroxy-2,2-dimethyl-6-isopropyl-2,3-dihydrobenzofuran The mixture of 5-acetoxy-4-t-butyl-2-hydroxy-6-isopropylbenzaldehyde and 5-acetoxy-6-t-butyl-2-hydroxy-4-isopropylbenzaldehyde was treated in the same manner as in Examples 19-4), 5) and 6) to give 171 mg of 6-t-butyl-5-hydroxy-2,2-dimethyl-4-isopropyl-2,3-dihydrobenzofuran as a white solid and 75 mg of 4-t-butyl-5-hydroxy-2,2-dimethyl-6-isopropyl-2,3-dihydrobenzofuran as a white solid.

Example 20-(1)

6-t-Butyl-5-hydroxy-2,2-dimethyl-4-isopropyl-2,3-dihydrobenzofuran $^1$H NMR (270 MHz, CDCl$_3$) δ ppm: 1.32 (d, 6H, J=7.3 Hz), 1.39 (s, 9H), 1.45 (s, 6H), 3.04 (s, 2H), 3.18 (septet, 1H, J=7.3 Hz), 4.39 (s, 1H), 6.59 (s, 1H).

Mass: 262 (M$^+$).

Example 20-(2)

4-t-Butyl-5-hydroxy-2,2-dimethyl-6-isopropyl-2,3-dihydrobenzofuran $^1$H NMR (270 MHz, CDCl$_3$) δ ppm: 1.29 (d, 6H, J=7.3 Hz), 1.30 (S, 9H), 1.43 (s, 6H), 2.95 (s, 2H), 3.09 (septet, 1H, J=7.3 Hz), 4.15 (s, 1H), 6.45 (s, 1H).

Mass: 262 (M⁺).

Table 1 shows structural formulae of compounds of the examples.

TABLE 1

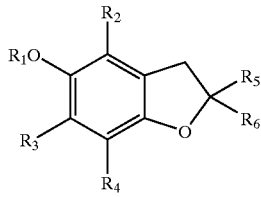

| Ex. Comp | R₁ | R₂ | R₃ | R₄ | R₅ | R₆ |
|---|---|---|---|---|---|---|
| 1 | H | t-Bu | H | t-Bu | H | H |
| 2 | H | t-Bu | H | t-Bu | Me | H |
| 3 | H | t-Bu | H | t-Bu | n-octyl | H |
| 4 | H | t-Bu | H | t-Bu | Me | Me |
| 5 | H | H | t-Bu | H | Me | Me |
| 6 | H | H | t-Bu | H | n-pentyl | n-pentyl |
| 7 | H | H | t-Bu | H | 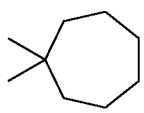 | |
| 8 | H | 2-propenyl | t-Bu | H | 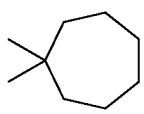 | |
| 9 | H | n-Pr | t-Bu | H | 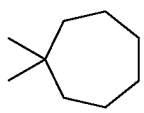 | |
| 10 | H | 2-methyl-2-propenyl | t-Bu | H | 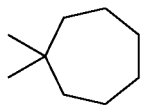 | |
| 11 | H | i-Bu | t-Bu | H | 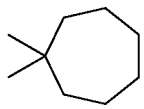 | |
| 12 | H | 1-methyl-2-propenyl | t-Bu | H | 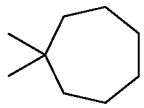 | |
| 13 | H | s-Bu | t-Bu | H | 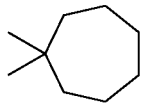 | |
| 14-(1) | H | Me | t-Bu | H | 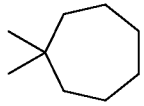 | |
| 14-(2) | H | Et | t-Bu | H | 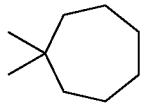 | |

TABLE 1-continued

| Ex. Comp | R₁ | R₂ | R₃ | R₄ | R₅ | R₆ |
|---|---|---|---|---|---|---|
| 15 | H | H | t-Bu | H | H | H |
| 16 | H | H | t-Bu | H | Me | H |
| 17 | H | i-Pr | i-Pr | H | Et | Et |
| 18 | H | i-Pr | i-Pr | H | Me | Me |
| 19 | H | Me | t-Bu | H | Me | Me |
| 20-(1) | H | i-Pr | t-Bu | H | Me | Me |
| 20-(2) | H | t-Bu | i-Pr | H | Me | Me |

Test Example 1

Protective Effect Against Cell Injury of Porcine Kidney-Derived LLC-PK1 Cells (1)

For the purpose of evaluating in vitro cytoprotective effect of the compounds of the present invention, protective effect against cell injury of porcine kidney-derived LLC-PK1 cells (ATCC-CRL-13921) induced by oxidized low-density lipoprotein (oxidized LDL) was examined. The oxidized LDL was prepared by placing 1 mg/ml of rabbit LDL in PBS (−) in the presence of 10 $\mu$W CuSO₄ at 37° C. for 24 hours. Cell cultures were prepared by inoculating $1.25 \times 10^4$ cells/250 $\mu$l/well on a 48-well plate using M199 medium containing 3% FBS. Test compounds were dissolved or suspended in ethanol and added at a ratio of 1.25 $\mu$l/well 16 hours before or immediately before addition of the oxidized LDL to a concentration of 0.1, 1 or 10 $\mu$M in each well. The oxidized LDL was diluted twice with physiological saline and then added to cells at 62.5 $\mu$l/well to a concentration of 100 $\mu$g/ml and the cells were incubated for 6 hours after addition of the oxidized LDL. After the incubation, 162.5 $\mu$l of the culture medium was collected from each of the wells and measured for the lactate dehydrogenase (LDH) activity (Lactate Dehydrogenase (LD-L): SIGNA DIAGNOSTICS) which has leaked into the culture medium.

The cytoprotective effect was expressed as a % cytoprotection where the effect in wells containing the oxidized LDL but without any test compound is 0% and the effect in wells containing physiological saline in place of the oxidized LDL is 100%.

Results are shown in Table 2.

TABLE 2

Protective Effect Against Cell Injury of Porcine Kidney-Derived LLC-PK1 Cells (1)

| Ex. Comp. No. | % cytoprotection[1] | | | % cytoprotection[2] | | |
|---|---|---|---|---|---|---|
| | 0.1 µM | 1 µM | 10 µM | 0.1 µM | 1 µM | 10 µM |
| 1 | 92.7 ± 6.8 | 104.1 + 1.4 | 100.5 + 0.3 | 17.5 ± 4.2 | 103.9 ± 3.2 | 102.3 ± 0.9 |
| 2 | 24.4 ± 16.2 | 101.2 ± 0.3 | 101.0 + 0.8 | 27.1 ± 9.5 | 101.5 ± 0.6 | 99.9 ± 1.0 |
| 5 | 77.6 + 15.0 | 103.4 ± 2.6 | 100.6 + 0.5 | 18.2 ± 5.4 | 100.8 ± 0.4 | 101.7 ± 0.5 | average ± standard deviation
[1]Test compounds added 16 hours before addition of oxidized LDL
[2]Test compounds added immediately before addition of oxidized LDL As shown in Table 2, the compounds of the present invention inhibit the cell injury induced by the oxidized LDL.

Test Example 2

Protective Effect Against Cell Injury of Porcine Kidney-Derived LLC-PK1 Cells (2)

For the purpose of evaluating in vitro cytoprotective effect of the compounds of the present invention, protective effect against cell injury of porcine kidney-derived LLC-PK1 cells (ATCC-CRL-13921) induced by oxidized low-density lipoprotein (oxidized LDL) was examined in the same manner as in Test Example 1.

Preparation of oxidized LDL and conditions for cell culture and addition of test compounds were the same as those in Test Example 1, except that the oxidized LDL was not diluted with physiological saline and added to cells at 25 µl/well to a concentration of 91 µg/ml and the cells were incubated for 6 hours after addition of oxidized LDL. After the incubation, 150 µl of the culture medium was collected from each of the wells and measured for the lactate dehydrogenase (LDH) activity (Lactate Dehydrogenase (LD-L): SIGMA DIAGNOSTICS) which has leaked in the culture medium. Results are shown in Table 3.

TABLE 3

Protective Effect Against Cell Injury of Porcine Kidney-Derived LLC-PK1 Cells (2)

| Ex. Comp. No. | % cytoprotection[1] | | | % cytoprotection[2] | | |
|---|---|---|---|---|---|---|
| | 0.1 µM | 1 µM | 10 µM | 0.1 µM | 1 µM | 10 µM |
| 4 | 11.3 ± 3.5 | 100.3 ± 0.3 | 98.3 ± 0.1 | 14.4 ± 0.6 | 99.0 ± 0.9 | 99.8 ± 0.3 |
| 7 | 19.1 ± 4.5 | 104.0 ± 0.6 | 104.6 ± 0.3 | 14.7 ± 1.2 | 104.3 ± 0.1 | 105.0 ± 0.5 |
| 9 | 12.9 ± 4.3 | 47.7 ± 11.4 | 103.8 ± 0.2 | 11.5 ± 0.7 | 58.9 ± 9.2 | 103.5 ± 0.5 |
| 11 | −2.7 ± 2.7 | 53.4 ± 11.8 | 101.8 ± 0.7 | −20.4 ± 4.0 | 88.7 ± 1.7 | 103.0 ± 0.6 |
| 12 | 15.5 ± 11.3 | 77.9 ± 11.8 | 102.2 ± 2.9 | −8.4 ± 3.8 | 79.4 ± 2.6 | 102.4 ± 0.4 |
| 13 | 5.5 ± 4.6 | 13.6 ± 1.2 | 100.4 ± 0.5 | 3.4 ± 0.5 | 9.9 ± 1.9 | 100.3 ± 0.6 |
| 14-(1) | −6.5 ± 1.8 | 103.1 ± 0.7 | 104.4 ± 0.5 | −9.2 ± 0.8 | 100.7 ± 0.3 | 102.9 ± 2.1 |
| 14-(2) | −14.3 ± 6.1 | 102.9 ± 0.9 | 103.9 ± 1.8 | −13.9 ± 0.8 | 99.4 ± 2.8 | 104.6 ± 1.0 |
| 16 | 12.7 ± 2.8 | 99.7 ± 0.6 | 103.2 ± 0.9 | 7.6 ± 2.5 | 90.8 ± 3.0 | 102.9 ± 1.2 |
| 17 | 40.5 ± 6.2 | 99.9 ± 3.1 | 99.0 ± 0.0 | 22.1 ± 0.7 | 101.0 ± 3.0 | 98.4 ± 0.3 |
| 18 | 12.1 ± 1.4 | 100.4 ± 0.3 | 100.5 ± 0.1 | −1.9 ± 3.2 | 99.7 ± 0.3 | 100.9 ± 0.4 |
| 19 | 31.1 ± 0.6 | 104.2 ± 1.4 | 102.0 ± 0.4 | 13.2 ± 2.4 | 101.9 ± 0.4 | 102.5 ± 0.5 |
| 20-(1) | −4.8 ± 4.5 | 100.0 ± 0.8 | 103.8 ± 1.4 | −24.0 ± 3.2 | 100.5 ± 0.7 | 100.1 ± 3.4 |
| 20-(2) | 95.3 ± 3.3 | 98.1 ± 0.5 | 97.3 ± 0.2 | 61.9 ± 24.5 | 97.8 ± 0.8 | 99.1 ± 0.9 | average ± standard deviation
[1]Test compounds added 16 hours before addition of oxidized LDL
[2]Test compounds added immediately before addition of oxidized LDL As shown in Table 3, the compounds of the present invention inhibit cell injury induced by the oxidized LDL.

Test Example 3

Protective Effect Against Cell Injury of Cultured Mesangial Cells

For the purpose of evaluating in vitro cytoprotective effect of the compounds of the present invention, protective effect against cell injury of cultured mesangial cells induced by oxidized low-density lipoprotein (LDL) was examined. The cells used were subcultures after 4 to 6 passages of the primary cultures of mesangial cells prepared from kidney of 4-week-old SD-strain male rats (Nippon Charles River Corp.).

The oxidized LDL was prepared by placing 1 mg/ml of rabbit LDL in PBS (−) in the presence of 10 µM $CuSO_4$ at 37° C. for 24 hours. Cell cultures were prepared by inoculating $2.5 \times 10^4$ cells/250 µl/well on a 48-well plate using RPMI1640 medium containing 20% FBS. Immediately before addition of test compounds, the medium was replaced with RPMI1640 free from FBS. Test compounds were dissolved or suspended in ethanol and added at 1.25 µl/well 16 hours before or immediately before addition of the oxidized LDL to a concentration of 1, 3 or 10 μM in each well. Unlike Test Example 1, the oxidized LDL was not diluted with physiological saline and added to cells at 25 μl/well to a concentration of 91 μg/ml and the cells were incubated for 8 hours after addition of the oxidized LDL. After the incubation, 150 μl of culture medium was collected from each of the wells and measured for the lactate dehydrogenase activity (Lactate Dehydrogenase (LD-L): SIGMA DIAGNOSTICS) which has leaked in culture medium.

The cytoprotective effect was expressed as a % cytoprotection where the effect in wells containing the oxidized LDL but without any test compound is 0% and the effect in wells containing physiological saline in place of the oxidized LDL is 100%.

Results are shown in Table 4.

TABLE 4

Protective Effect against Cell Injury of Cultured Mesangial Cells

| Ex. Comp. No. | % cytoprotection[1] | | % cytoprotection[1] | |
|---|---|---|---|---|
|  | 1 μM | 3 μM | 1 μM | 3 μM |
| 1 | 24.2 ± 9.3 | 78.2 ± 13.4 | 40.3 ± 3.2 | 69.7 ± 13.3 |
| 2 | 35.6 ± 7.5 | 60.5 ± 6.2 | 40.6 ± 8.2 | 53.1 ± 5.7 |
| 4 | 31.1 ± 5.4 | 66.4 ± 5.9 | 32.5 ± 1.9 | 54.3 ± 9.7 |
| 5 | 34.2 ± 4.5 | 42.3 ± 4.7 | 11.3 ± 2.4 | 28.9 ± 2.0 |
| 7 | 19.3 ± 2.8 | 18.1 ± 4.1 | 22.0 ± 1.9 | 24.5 ± 0.8 |
| 9 | 14.4 ± 5.1 | 56.2 ± 9.3 | 29.6 ± 2.0 | 46.3 ± 1.7 |
| 11 | −3.5 ± 9.1 | 13.8 ± 7.8 | 4.8 ± 5.1 | 41.3 ± 1.0 |
| 12 | 11.8 ± 2.6 | 37.9 ± 8.3 | 17.4 ± 4.0 | 42.8 ± 3.7 |
| 13 | 1.7 ± 2.9 | 18.4 ± 9.2 | −4.3 ± 5.1 | 11.1 ± 4.3 |
| 14-(1) | 6.6 ± 8.4 | 52.7 ± 14.3 | 23.1 ± 1.2 | 45.6 ± 1.8 |
| 14-(2) | 19.7 ± 7.7 | 59.3 ± 2.1 | 34.4 ± 1.5 | 43.2 ± 2.8 |
| 15 | −4.0 ± 3.5 | 33.6 ± 11.5 | −14.6 ± 3.3 | 5.4 ± 5.1 |
| 16 | 50.6 ± 5.9 | 45.3 ± 9.4 | 18.7 ± 1.3 | 28.3 ± 6.2 | average ± standard deviation
[1]Test compounds added 16 hours before addition of oxidized LDL
[2]Test compounds added immediately before addition of oxidized LDL As shown in Table 4, the compounds of the present invention inhibit cell injury induced by the oxidized LDL.

INDUSTRIAL APPLICABILITY OF THE INVENTION 2,3-Dihydrobenzofuran derivatives of the present invention show a potent cytoprotective effect against cell injury induced by oxidized LDL in kidney-derived cell cultures, so that they are useful as therapeutic or prophylactic agents for renal diseases such as chronic renal failure, diabetic nephrosis, glomerular nephritis, immunocomplex nephritis, acute renal failure, nephropathies caused by platinum complex-based anticancer agents such as cisplatin or other drugs such as gentamicin, nephropathies caused by agrichemicals such as Paracort, uremia, etc. They are also useful as organ preservatives.

What is claimed is:

1. A compound of formula (1):

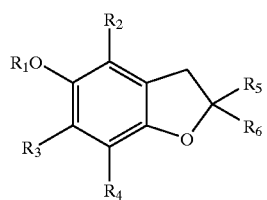

(1)

wherein $R_1$ represents a hydrogen atom or an optionally substituted acyl group, $R_2$, $R_3$ and $R_4$, which may be identical or different, each represents a hydrogen atom, a lower alkyl group or a lower alkenyl group, provided that one or the other of $R_2$ and $R_3$, but not both simultaneously, is t-butyl, and that $R_2$ is not sec-butyl when $R_3$ is t-butyl, and $R_5$ and $R_6$ combine to form a cycloalkyl group or a saturated heterocyclic group containing one or more oxygen atoms or sulfur atoms, or an optically active isomer or a pharmaceutically acceptable salt thereof.

2. The compound of claim 1, wherein $R_1$ represents a hydrogen atom or an optionally substituted acyl group containing 1 to 7 carbon atoms, and $R_5$ and $R_6$ combine to form a cycloalkyl group containing 3 to 8 carbon atoms or a saturated 5–12 membered heterocyclic group containing 1 to 3 oxygen atoms or sulfur atoms.

3. The compound of claim 2, wherein $R_1$ represents a hydrogen atom.

4. The compound of claim 1, which is represented by formula (2):

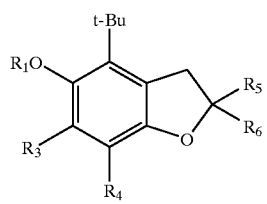

(2)

wherein $R_4$ represents a hydrogen atom or a t-butyl group, and $R_1$, $R_3$, $R_5$ and $R_6$ have the same meanings as defined in claim 1.

5. The compound of claim 4, wherein $R_1$ represents a hydrogen atom or an optionally substituted acyl group containing 1 to 7 carbon atoms, and $R_5$ and $R_6$ combine to form a cycloalkyl group containing 3 to 8 carbon atoms or a saturated 5–12 membered heterocyclic group containing 1 to 3 oxygen atoms or sulfur atoms.

6. The compound of claim 5, wherein $R_1$ represents a hydrogen atom.

7. The compound of claim 1, which is represented by formula (3):

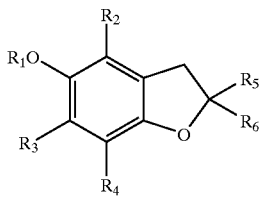

(3)

wherein $R_1$, $R_2$, $R_5$ and $R_6$ have the same meanings as defined in claim 1.

8. The compound of claim 7, wherein $R_1$ represents a hydrogen atom or an optionally substituted acyl group containing 1 to 7 carbon atoms, and $R_5$ and $R_6$ combine to form a cycloalkyl group containing 3 to 8 carbon atoms or a saturated 5–12 membered heterocyclic group containing 1 to 3 oxygen atoms or sulfur atoms.

9. The compound of claim 8, wherein $R_1$ represents a hydrogen atom.

10. A method of treating renal diseases comprising administering to a patient having a renal disease an effective amount of a compound of the formula (1):

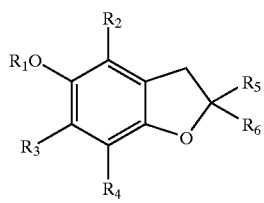

(1)

wherein $R_1$ represents a hydrogen atom or an optionally substituted acyl group, $R_2$, $R_3$ and $R_4$, which may be identical or different, each represents a hydrogen atom, a lower alkyl group or a lower alkenyl group, provided that one or the other of $R_2$ and $R_3$, but not both simultaneously, is t-butyl, and that $R_2$ is not sec-butyl when $R_3$ is t-butyl, and $R_5$ and $R_6$ combine to form a cycloalkyl group or a saturated heterocyclic group containing one or more oxygen atoms or sulfur atoms, or an optically active isomer or a pharmaceutically acceptable salt thereof.

11. The method in accordance with claim 10, wherein, in said compound of formula (1), $R_1$ represents a hydrogen atom or an optionally substituted acyl group containing 1 to 7 carbon atoms, and $R_5$ and $R_6$ combine to form a cycloalkyl group containing 3 to 8 carbon atoms or a saturated 5–12 membered heterocyclic group containing 1 to 3 oxygen atoms or sulfur atoms.

12. The method in accordance with claim 10, wherein the renal disease is selected from the group consisting of chronic renal failure, diabetic nephrosis, glomerular nephritis, immunocomplex nephritis, acute renal failure, nephropathies caused by drugs or agrochemicals, and uremia.

13. A method of preserving organs comprising storing an organ in an organ preservative containing an effective amount of a compound of formula (1):

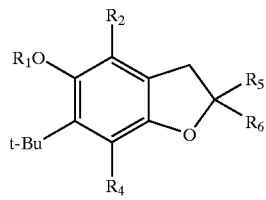

(1)

wherein $R_1$ represents a hydrogen atom or an optionally substituted acyl group, $R_2$, $R_3$ and $R_4$, which may be identical or different, each represents a hydrogen atom, a lower alkyl group or a lower alkenyl group, provided that one or the other of $R_2$ and $R_3$, but not both simultaneously, is t-butyl, and that $R_2$ is not sec-butyl when $R_3$ is t-butyl, and $R_5$ and $R_6$ combine to form a cycloalkyl group or a saturated heterocyclic group containing one or more oxygen atoms or sulfur atoms, or an optically active isomer or a pharmaceutically acceptable salt thereof.

14. The method in accordance with claim 13, wherein, in said compound of formula (1), $R_1$ represents a hydrogen atom or an optionally substituted acyl group containing 1 to 7 carbon atoms, and $R_5$ and $R_6$ combine to form a cycloalkyl group containing 3 to 8 carbon atoms or a saturated 5–12 membered heterocyclic group containing 1 to 3 oxygen atoms or sulfur atoms.

15. The method in accordance with claim 13, wherein the organ to be preserved is kidney.

16. The method in accordance with claim 13, wherein said compound is dissolved in said maintenance solution at a concentration of 0.1–10,000 mg/L.

17. The method in accordance with claim 12, wherein the nephropathy caused by drugs or agrochemicals is that caused by platinum complex-based anticancer agents or gentamicin.

18. A compound in accordance with claim 1, wherein $R_2$ and $R_3$ each represent a hydrogen atom, a lower alkyl group other than sec-butyl or a lower alkenyl group, with the proviso that one or the other of $R_2$ and $R_3$, but not both simultaneously, is t-butyl.

19. A compound in accordance with claim 1, wherein one of $R_2$ and $R_3$ is t-butyl and the other is selected from the group consisting of a hydrogen atom and a methyl, ethyl, propyl or lower alkenyl group.

20. A method in accordance with claim 10, wherein, in said compound of formula (1), $R_2$ and $R_3$ each represent a hydrogen atom, a lower alkyl group other than sec-butyl or a lower alkenyl group, with the proviso that one or the other of $R_2$ and $R_3$, but not both simultaneously, is t-butyl.

21. A method in accordance with claim 10, wherein, in said compound of formula (1), one of $R_2$ and $R_3$ is t-butyl and the other is selected from the group consisting of a hydrogen atom and a methyl, ethyl, propyl or lower alkenyl group.

22. A method in accordance with claim 13, wherein, in said compound of formula (1), $R_2$ and $R_3$ each represent a hydrogen atom, a lower alkyl group other than sec-butyl or a lower alkenyl group, with the proviso that one or the other of $R_2$ and $R_3$, but not both simultaneously, is t-butyl.

23. A method in accordance with claim 13, wherein, in said compound of formula (1), one of $R_2$ and $R_3$ is t-butyl and the other is selected from the group consisting of a hydrogen atom and a methyl, ethyl, propyl or lower alkenyl group.

* * * * *